(12) United States Patent  
Bhatia et al.

(10) Patent No.: US 9,194,841 B2  
(45) Date of Patent: Nov. 24, 2015

(54) DEVICES AND PROCESSES FOR ANALYZING NUCLEIC ACID DAMAGE AND REPAIR USING ELECTROPHORESIS

(75) Inventors: Sangeeta N. Bhatia, Lexington, MA (US); Bevin P. Engelward, Lexington, MA (US); David K. Wood, Cambridge, MA (US); David M. Weingeist, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 440 days.

(21) Appl. No.: 13/547,708

(22) Filed: Jul. 12, 2012

(65) Prior Publication Data

US 2012/0277118 A1    Nov. 1, 2012

Related U.S. Application Data

(63) Continuation of application No. 12/431,287, filed on Apr. 28, 2009, now abandoned.

(60) Provisional application No. 61/049,545, filed on May 1, 2008.

(51) Int. Cl.
*G01N 27/447* (2006.01)
*B01L 3/00* (2006.01)

(52) U.S. Cl.
CPC .... *G01N 27/44782* (2013.01); *B01L 3/502715* (2013.01); *B01J 2219/0043* (2013.01);
(Continued)

(58) Field of Classification Search
CPC ............. B01J 2219/0043; B01J 2219/00743; B01J 2219/00662; B01J 2219/00637; B01J 2219/00527; B01J 2219/00317; B01L 2400/0421; B01L 2300/0819; B01L 3/502715; G01N 27/44782
See application file for complete search history.

(56) References Cited

U.S. PATENT DOCUMENTS 4,695,548 A    9/1987 Cantor et al.
5,976,813 A *  11/1999 Beutel et al. ............ 506/7
(Continued)

FOREIGN PATENT DOCUMENTS

WO    WO-9210092 A1    6/1992
WO    WO-9930154 A2    6/1999
(Continued)

OTHER PUBLICATIONS

J. Rettig et al., Large-Scale Single-Cell Trapping and Imaging Using Microwell Arrays, Anal. Chem., vol. 77, pp. 5628-5634.*
(Continued)

*Primary Examiner* — J. Christopher Ball
*Assistant Examiner* — Maris R Kessel
(74) *Attorney, Agent, or Firm* — Nutter McClennen & Fish LLP

(57) ABSTRACT

Systems, methods, and devices are provided for assessing DNA damage and repair in cells by measuring DNA migration under electrophoresis. In one exemplary embodiment, a microarray configured to hold cells in a predetermined spatial relationship is employed to improve accuracy, speed, and reliability of such measurements. In another embodiment, a self-contained cassette having a matrix material disposed therein can be used to create a substantially uniform environment for analyzing DNA damage and repair. Fluid can be circulated through the cell to assist in creating spatial patterns on the matrix material, or alternatively, the matrix material can already include a microarray pattern disposed thereon. Various methods and systems that take advantage of such microarrays and cassettes are also provided.

17 Claims, 12 Drawing Sheets

(52) U.S. Cl.
CPC ............ *B01J2219/00317* (2013.01); *B01J 2219/00527* (2013.01); *B01J 2219/00605* (2013.01); *B01J 2219/00612* (2013.01); *B01J 2219/00637* (2013.01); *B01J 2219/00662* (2013.01); *B01J 2219/00743* (2013.01); *B01L 2300/069* (2013.01); *B01L 2300/0809* (2013.01); *B01L 2300/0819* (2013.01); *B01L 2400/049* (2013.01); *B01L 2400/0421* (2013.01)

(56) References Cited

U.S. PATENT DOCUMENTS

| | | | |
|---|---|---|---|
| 6,379,516 B1* | 4/2002 | Cabilly | B01D 57/02 204/450 |
| 6,403,367 B1 | 6/2002 | Cheng et al. | |
| 6,562,213 B1 | 5/2003 | Cabilly et al. | |
| 2005/0169962 A1 | 8/2005 | Bhatia et al. | |
| 2006/0068408 A1 | 3/2006 | Witte et al. | |
| 2007/0166713 A1 | 7/2007 | Frieauff | |
| 2009/0272657 A1 | 11/2009 | Bhatia et al. | |

FOREIGN PATENT DOCUMENTS

| | | |
|---|---|---|
| WO | WO-0136958 A1 | 5/2001 |
| WO | WO-0218901 A2 | 3/2002 |

OTHER PUBLICATIONS

Albrecht DR, Underhill GH, Wassermann TB, Sah RL, Bhatia SN (2006) Probing the role of multicellular organization in three-dimensional microenvironments. Nat Methods 3(5): 369-375.
Bhatia SN, Yarmush ML, Toner M (1997) Controlling cell interactions by micropatterning in co-cultures: hepatocytes and 3T3 fibroblasts. J Biomed Mater Res 34(2): 189-199.
Chin VI, Taupin P, Sanga S, Scheel J, Gage FH et al. (2004) Microfabricated platform for studying stem cell fates. Biotechnol Bioeng 88(3): 399-415.
Dong M, Dedon PC (2006) Relatively small increases in the steady-state levels of nucleobase deamination products in DNA from human TK6 cells exposed to toxic levels of nitric oxide. Chem Res Toxicol 19(1): 50-57.
Flaim CJ, Chien S, Bhatia SN (2005) An extracellular matrix microarray for probing cellular differentiation. Nat Methods 2(2): 119-125.
Rettig JR, Folch A. (2005) Large-scale single-cell trapping and imaging using microwell arrays. Anal Chem. 77(17):5628-34.
Horvathova E, Slamenova D, Gabelova A (1999) Use of single cell gel electrophoresis (comet assay) modifications for analysis of DNA damage. Gen Physiol Biophys 18 Spec No. 70-74.
Kiskinis E, Suter W, Hartmann A (2002) High throughput Comet assay using 96-well plates. Mutagenesis 17(1): 37-43.
Kiziltepe T, Yan A, Dong M, Jonnalagadda VS, Dedon PC et al. (2005) Delineation of the chemical pathways underlying nitric oxide-induced homologous recombination in mammalian cells. Chem Biol 12(3): 357-369.
Leong, Jen, et al. (2009) "Single-Cell Patterning and Adhesion on Chemically Engineered Poly(dimethylsiloxane) Surface." Langmuir. [published on web].
Liu VA, Shatia SN (2002) Three-dimensional photopatterning of hydrogels containing living cells. Biomed Microdev 4: 257-266.
Moeller, Khademhossein, et al. (2008) "A microwell array system for stem cell culture." Biomaterials. vol. 29|6:752-763.
Pouget JP, Douki T, Richard MJ, Cadet J (2000) DNA damage induced in cells by gamma and UVA radiation as measured by HPLC/GC-MS and HPLC-EC and Comet assay. Chem Res Toxicol 13(7): 541-549.
Pouget JP, Ravanat JL, Douki T, Richard MJ, Cadet J (1999) Measurement of DNA base damage in cells exposed to low doses of gamma-radiation: comparison between the HPLC-EC and comet assays. Int J Radiat Biol 75(1): 51-58.
Ritter D, Knebel J (2009) Genotoxicity testing in vitro—Development of a higher throughput analysis method based on the comet assay. Toxicology in Vitro, In Press.
Rosenthal A, Macdonald A, Voldman J. (2007) Cell patterning chip for controlling the stem cell microenvironment. Biomaterials 28(21):3208-16.
Stang A, Witte I (2009) Performance of the comet assay in a high-throughput version. Mutation Research/Genetic Toxicology and Environmental Mutagenesis 675: 5-10.
Trzeciak, Evans, et al. (2008) "A Modified Alkaline Comet Assay for Measuring DNA Repair Capacity in Human Populations." Radiat. Res. vol. 169:110-121.
Moller P (2006) The alkaline comet assay: towards validation in biomonitoring of DNA damaging exposures. Basic Clin Pharmacol Toxicol 98(4): 336-345.
Spanswick, Victoria, John Hartley, et al. (2008) "Measurement of Drug-Induced DNA Interstrand Crosslinking Using the Single-Cell Gel Electrophoresis Assay." *Methods in Molecular Medicine*. vol. 28: 143-154.
Trevigen CometAssay 96, as found at <http://www.trevigen.com/dnadamage/cometassay96.php>, including protocol associated therewith.
Trevigen Higher Throughput CometAssay, as found at <http://www.trevigen.com/dnadamage/cometassayHT.php>, including protocol associated therewith.
International Search Report for PCT/US09/041931, dated Sep. 2, 2009.
International Preliminary Report and Written Opinion, dated Nov. 2, 2010, 8 pages.

* cited by examiner

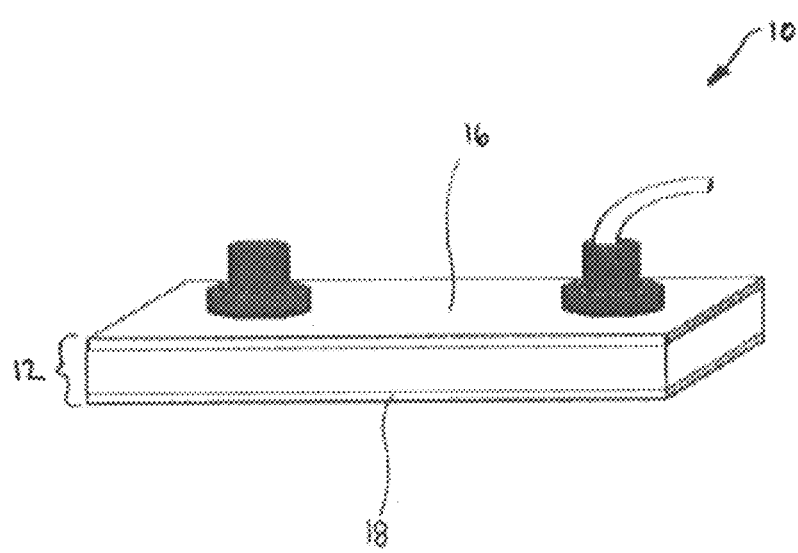

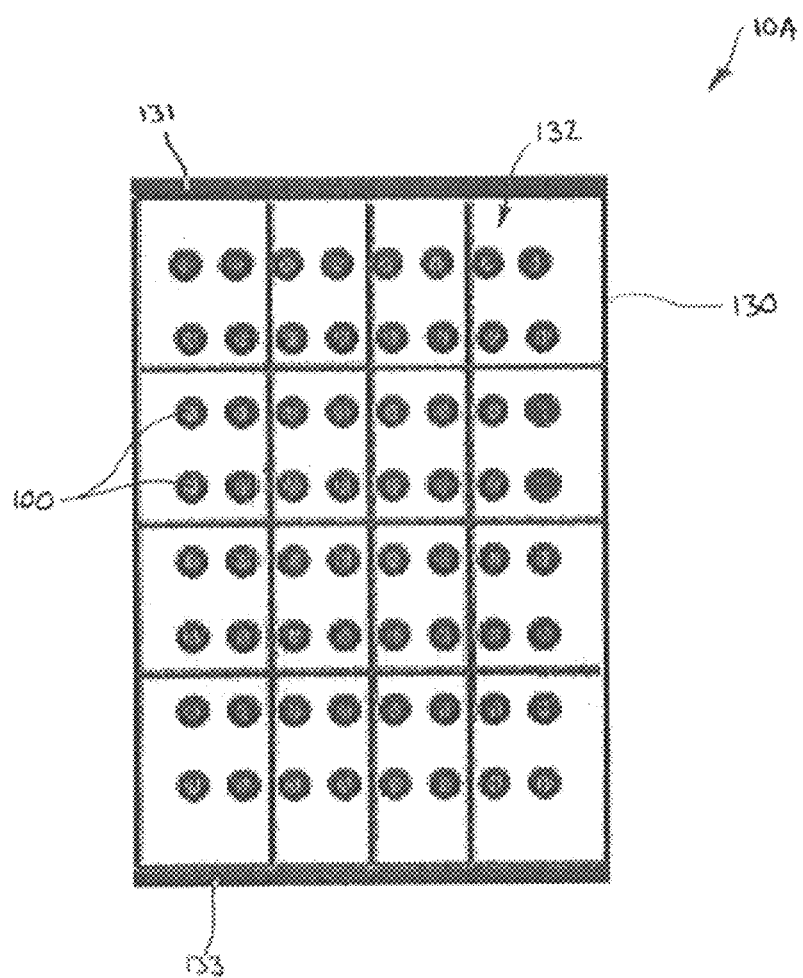

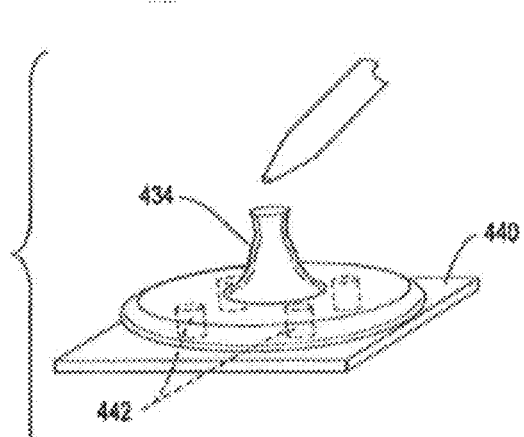
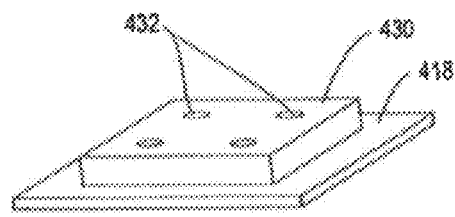
FIG. 8A     FIG. 8B
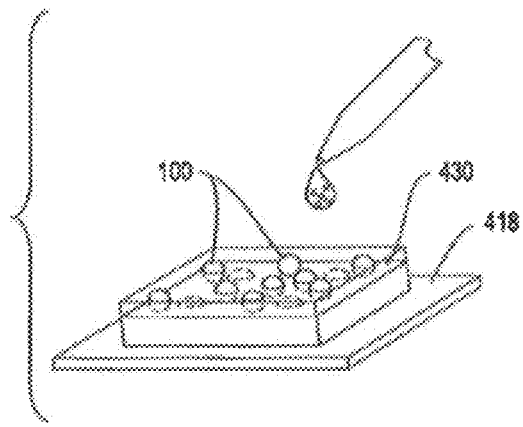
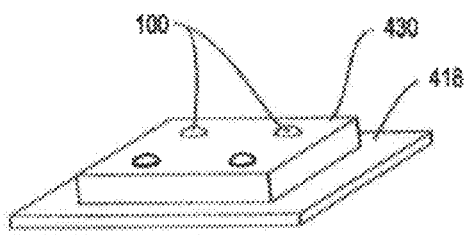
FIG. 8C     FIG. 8D
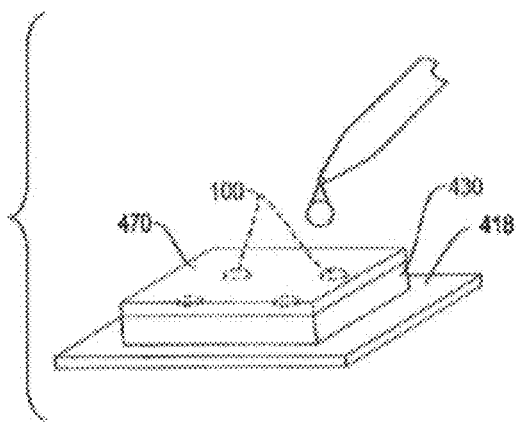
FIG. 8E

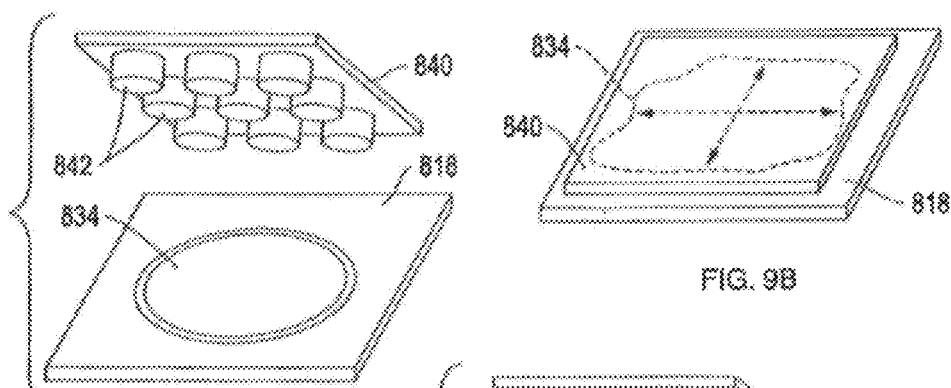
FIG. 9A
FIG. 9B
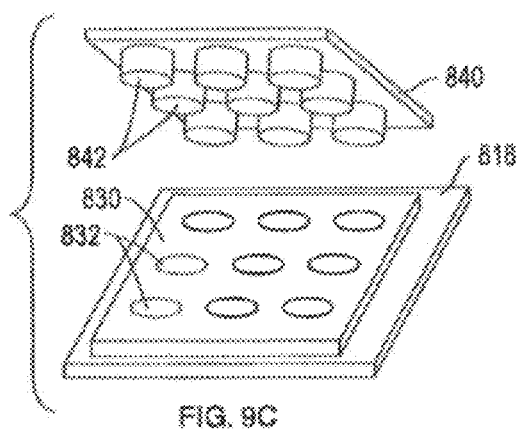
FIG. 9C
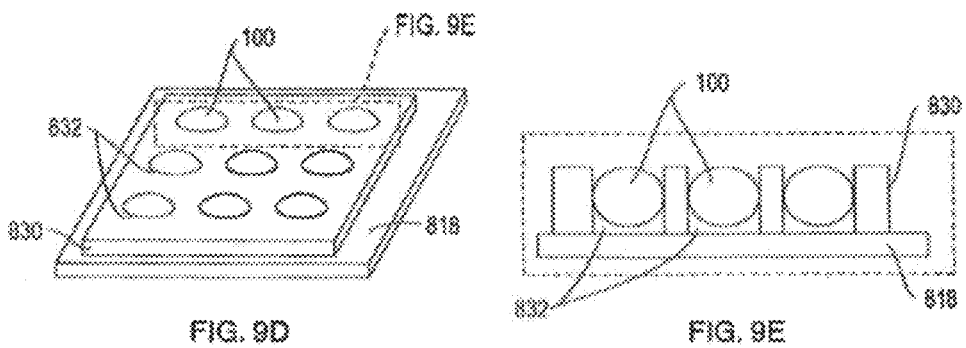
FIG. 9D
FIG. 9E
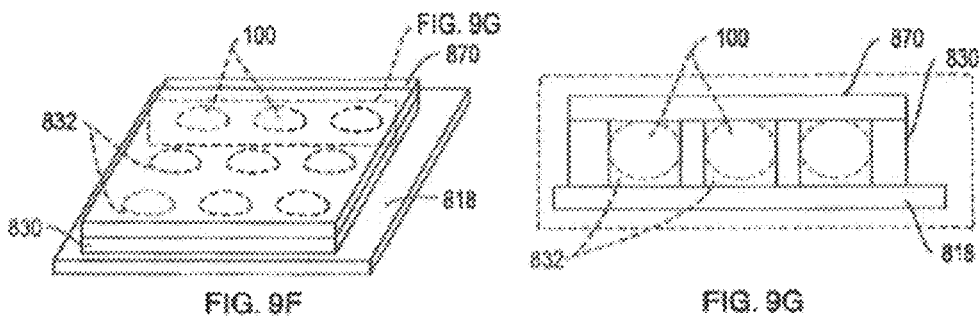
FIG. 9F
FIG. 9G

DEVICES AND PROCESSES FOR ANALYZING NUCLEIC ACID DAMAGE AND REPAIR USING ELECTROPHORESIS

PRIORITY

The present invention claims priority to U.S. patent application Ser. No. 12/431,287, entitled "Devices and Processes for Analyzing Nucleic Acid Damage and Repair Using Electrophoresis" and filed on Apr. 28, 2009, which claims priority to U.S. Provisional Application No. 61/049,545, entitled "Devices and Processes for Analyzing Nucleic Acid Damage and Repair Using Electrophoresis" and filed on May 1, 2008, both of which are hereby incorporated by reference in their entireties.

GOVERNMENT RIGHTS

This invention was made with government support under Grant Nos. U01-ES016045 and P30-ES002109 awarded by the National Institutes of Health. The government has certain rights in this invention.

TECHNICAL FIELD

The present invention generally relates to devices and processes for analyzing nucleic acid damage and repair, and more particularly is directed to systems, devices, and processes for analysis of nucleic acids using electrophoresis.

BACKGROUND

Environmentally and endogenously-induced nucleic acid damage, and in particular deoxyribonucleic acid ("DNA") damage, has long been associated with cancer, aging, neurological disorders, and heritable diseases. Measurements of DNA damage in human samples is therefore fundamentally valuable, both for delineating genotoxic environmental conditions that render cells vulnerable to mutations, and for revealing genetic factors that modulate susceptibility to DNA damage. For example, it is well established that heritable DNA repair deficiencies can promote cancer. (Vogelstein and Kinzler 2004.)

Although it is generally accepted that environmental conditions can induce DNA damage that is hazardous to human health, and that people deficient in the ability to repair DNA damage are more prone to diseases, measurement of DNA damage and repair in human samples is far from routine. Despite the multitude of industrial chemicals present in today's workplaces, environment, air, food, and water, fewer than 1000 such chemicals have been thoroughly characterized in terms of the risks that they pose to human health. This is at least because existing assays are labor-intensive, expensive, and technically challenging.

Many different approaches for analyzing nucleic acid damage and repair presently exist, but they each have their own distinct shortcomings. Many assays require the cells be homogenized in order to isolate and analyze DNA. This process makes it impossible to know which cell types are the most damaged unless cell types are separated prior to analysis. Further, in mixed samples, if there are rare highly-damaged cells, their presence can be obscured by the numerous cells that harbor low levels of DNA lesions. Knowledge about how a minority population of cells responds to DNA damage can have important implications, as it only takes one highly damaged cell to initiate cancer or many other diseases.

Another problem many laboratories encounter is that the handling and/or processing of a sample of cells, or a tissue, can introduce DNA damage. For example, when tissue is disaggregated, the levels of DNA damage increase as a result of the stresses involved in tissue disaggregation.

One approach used for assessing the extent of DNA repair is the use of unscheduled DNA synthesis. However, this approach is not useful for assessing directly-induced DNA damage, such as double and single strand breaks.

Structural and numerical chromosome aberrations, as well as sister chromatid exchanges, are alternative ways of detecting damage in DNA, but they can only analyze cells that are in metaphase. Accordingly, some cell types can almost never be analyzed because they rarely are in metaphase, while for all cell types enough cells in metaphase must be gathered while cells in any other phase must be discarded. Further, with respect to structural and numerical chromosome aberrations, information linking the observed aberration back to the cell in which it occurred is nearly impossible to gain because once a metaphase spread is made, cell type information is generally lost. The process is also very slow and labor-intensive, generally requiring extensive microscope time and skilled technicians. It is also not feasible to detect subtle effects of DNA repair deficits or exposures using the aberration method unless sufficient time has elapsed for accumulation of rare aberrations, which in many cases is too late for appropriate intervention to occur. With respect to the sister chromatid exchanges, they are highly transient in nature, so the timing relative to a potential exposure is critical, which in turn makes "false negative" readings a common occurrence.

Micronucleus assays are used to detect DNA fragmentation. While micronucleus assays can be useful for studies of one organ, such as bone marrow, they are of limited value for many other cell types. Further, the assays cannot be used to assess DNA base lesions.

Prior to the present disclosure, three of the more promising methods for DNA damage detection were mass spectrometry, immunohistochemical detection of phosphorylated H2AX, and the comet assay. Mass spectrometry can be useful for precision lesion identification, but at present this approach is not readily amenable to large scale population studies due to the number of cells needed per assay, the technical difficulty of performing the assay, and the cost of the equipment required for analysis. Currently it takes about two weeks to process a set of approximately ten samples. Even under optimal conditions, this approach requires technical expertise and access to a mass spectrometer.

While immunohistochemical detection of phosphorylated H2AX is a sensitive way for measuring DNA double strand breaks, it is technically very difficult to use this assay to assess DNA damage levels in S phase cells. (MacPhail et al. 2003; Han et al. 2006.) It is really only optimal for cells in the G0 or G1 phases, and because many environmental exposures that cause genomic instability do so by interfering with DNA replication during the S phase, this is problematic. This method is further limited by the fact that it only detects double strand breaks. While these are clearly very important lesions, in the case of ultraviolet and aflatoxin exposure, which are two of the best-characterized environmental mutagens, the vast majority of the DNA lesions created by these exposures are base-modifications, not double strand breaks. (Friedberg et al. 2006.)

The comet assay is also a sensitive assay for measuring both the levels of DNA damage and the rate of DNA repair. In a comet assay, cells are generally embedded in agarose, and after electrophoresis is performed on the assay, undamaged DNA generally remains supercoiled and highly compact while damaged DNA more readily migrates during electrophoresis and gives rise to the appearance of a bright nucleoid with a comet-like tail. Unfortunately, using standard methods and/or devices, it takes hours to prepare and process just a single sample. It is a very labor and time-intensive process. For example, completing the incubation steps alone can take approximately four hours. This is due, at least in part, to the fact that current comet assays are performed at room temperature. Further, the feasibility of testing multiple conditions in parallel and/or processing a number of independent samples is severely limited by the current methods and devices. This is due, at least in part, to the potential of overlapping tails of cells being tested. In terms of the area required for a routine comet assay, the density of the cells is primarily limited by interference between cells. Another problem with current comet assays is that there is a lack of standardization that has lead to undesirable variability not only from laboratory-to-laboratory, but from user-to-user from the same laboratory and from slide-to-slide and assay-to-assay from the same user.

At present, clinical assays are not generally available to medical doctors to assess a patient's DNA repair capacity. This information would be invaluable to a person who might be able to avoid cancer simply by avoiding certain exposures. Furthermore, a person's DNA repair information could be used to guide appropriate intervals for cancer screening, such as for early detection of cancers, and even could be used to guide appropriate choices of treatments, for example by preventing chemotherapy-induced lethality in a repair-deficient patient. Aside from cancer, knowledge of a person's DNA repair capacity could guide appropriate selection of other pharmaceuticals to avoid drugs to which a person may be acutely sensitive. Having an assay that directly measures an endpoint that is predictive of how a person would respond to environmental risk factors would also be extremely valuable, which in turn would allow a person to avoid risky behaviors and allow physicians to more accurately weigh the cost-benefit of anti-inflammatory interventions, such as non-steroidal anti-inflammatory drugs. It would be an invaluable tool for both revealing and controlling environmental risk factors. Further, in the research setting, a high-throughput DNA repair assay would be useful for the Gene-Environment Initiative because it could be used to identify as-yet-unknown genetic risk factors that cause a deficiency in DNA repair and thus sensitize particular individuals to certain environmental exposures.

Accordingly, there exists a need for a sensitive, efficient, consistent, and reliable method for analyzing nucleic acid damage and repair in all cell cycle phases. Likewise, there exists a need for devices and systems capable of carrying out a sensitive, efficient, consistent, and reliable analysis of nucleic acid damage and repair in all cell cycle phases. Additional benefits could be realized if such methods, devices, and systems allowed for parallel processing to permit simultaneous analysis of a multitude of samples or conditions.

SUMMARY OF THE INVENTION

Systems, methods, and apparatuses are disclosed for assessing DNA damage and repair in cells by measuring DNA migration under electrophoresis. In one aspect, microarrays capable of holding cells in predetermined spatial locations are employed to improve accuracy and reproducibility of the measurements. Self-contained cassettes can include a matrix material, such as agarose, and a fluid circulation path to situate the cells in a spatial pattern in or on the matrix material such that precise image analysis can be performed following electrophoresis. The methods and apparatuses can be used, for example, to measure DNA damage, DNA repair rates, and the response of various cell types to radiation or chemotherapeutic agents.

One exemplary embodiment of an apparatus is a self-contained assay cassette having a housing that defines an inner cavity. A matrix material can be disposed within the cavity and can include a plurality of cell assay locations. The cassette can further include an opening for introducing cells into the cavity such that when the cells are introduced into the cavity, the cells are distributed to the cell assay locations of the matrix material. In one embodiment the opening is a fluid delivery inlet port configured to deliver a fluid into the cavity. Alternatively, the opening can be a portion of the housing that is capable of being opened, such as by removal of a portion of the housing. The cassette can also include a fluid delivery outlet port that is configured to remove a fluid from the cavity. The housing can include a plurality of layers with any number of components, or no components at all, disposed in between the layers. In one embodiment a gasket can be disposed between the layers, while in another embodiment a membrane can be disposed between the layers. The housing can be any number of heights, including in the range of about 25 micrometers to about 1 millimeter.

The matrix material can be any substance configured to allow the cells to migrate as a result of electrophoresis, but in one exemplary embodiment the matrix material is an agarose gel. Ideally, the matrix material has a desired thickness that is generally uniform and can range, for example, from about 10 to about 500 micrometers. In an exemplary embodiment, the cell assay locations are at a uniform height such that cells located in the cell assay locations can likewise be at a uniform height. The matrix material can also include one or more cell capture sites. In one embodiment, the cell capture sites are recesses formed in the matrix material. The cassette can also include one or more dividers to separate portions of the matrix material disposed in the housing. In another embodiment the cassette can include one or more electrode terminals for applying an electric current to the matrix material disposed therein. In one exemplary embodiment the cassette has two electrode terminals. The self-contained electrophoresis assay cassette can be disposable.

An exemplary embodiment of a matrix material can include a gel-like substance and an array of sites that are configured to capture cells for use in analyzing a nucleic acid. The gel-like substance can be any number of substances, but in a preferred embodiment it is an agarose gel. The sites can be in a variety of shapes, patterns, and sizes, and can be spaced in a number of different manners. For example, the sites can include a plurality of recesses, troughs, and/or microwells, and can be in the shape of a grid or other desired pattern. In one embodiment, the sites are proximal to the surface of the gel-like substance.

One embodiment of a system for nucleic acid analysis includes a receptacle configured to receive a multi-site matrix material that has a plurality of cell assay locations configured to receive cells. The receptacle can provide a frame of reference for spatial differentiation of the matrix material. The system can further include a first applicator for applying a first reagent to at least a portion of the matrix material and a second applicator for applying a second reagent to at least a second portion of the matrix material. The first and second reagent can be the same or different reagents, and the first and second portions of the matrix material can include part of the same portions of the matrix material or can be entirely different portions. In one embodiment of the system the second applicator can be configured to apply the second reagent to a portion of the matrix material that is distinct from the portion to which the first reagent is applied, while in another embodiment of the system the second applicator can be configured to apply the second reagent to a portion of the matrix material that at least partially overlays the portion to which the first reagent is applied. In one exemplary embodiment the matrix material is an agarose gel. The matrix material can include one or more cell capture sites disposed on the matrix material. In one embodiment, the cell capture sites are recesses formed in the matrix material. The system can further include a shunt coupled to the receptacle such that the receptacle is configured to receive a cell containing fluid through the shunt, thus allowing the cell to be analyzed by the receptacle. The receptacle can optionally be disposable.

In another embodiment of a system for nucleic acid analysis, the system includes a multi-site matrix material having a plurality of cell assay locations configured to receive cells on the matrix material and a reagent-applying overlay that is disposed above the matrix material. The overlay can be configured to apply at least one reagent to at least a portion of the plurality of cell assay locations. In one embodiment the overlay includes a plurality of macrowells. One or more drug-bearing hydrogels can be disposed in the macrowells. In another embodiment, the plurality of cell assay locations can be configured to receive cells from a plurality of sources. In one embodiment the sources are similar cells from different subjects, such as different humans. In another embodiment the sources are different cell types from the same subject, such as the same human. In still another embodiment the sources are different cell types from different subjects, such as different humans.

A system for determining multiple exposure conditions can include a multi-site matrix material having a plurality of cell assay locations configured to receive cells on the matrix material and a template disposed above the multi-site matrix material. The template can be configured to selectively regulate exposures of the cell assay locations to one or more conditions. In one embodiment the template is a moveable shield. The shield can be made of lead. The conditions that the cell assay locations are exposed to can be created from any number of sources, but in one exemplary embodiment the conditions are created by an electromagnetic radiation source, such as an x-ray machine.

One exemplary embodiment of a method for analyzing a nucleic acid includes disposing a plurality of cells in a self-contained electrophoresis assay cassette that has a matrix material disposed inside, performing electrophoresis on the cells, and analyzing parameters resulting from performing the electrophoresis. The method can include introducing a fluid into the cassette to diffuse the cells across at least a portion of the matrix material. When fluid is introduced into the cassette, the method can also include evacuating the fluid from the cassette. When the cells are diffused, in one exemplary embodiment the cells diffuse in a substantially downward direction.

In another exemplary embodiment of a method for analyzing a nucleic acid, a matrix material that is capable of receiving a plurality of cells is obtained, at least one cell is disposed in each of a plurality of cell assay locations, the cells are exposed to at least one reagent, electrophoresis is performed on the plurality of cells, and parameters that result from the electrophoresis are analyzed. The reagent can be any number of reagents, but preferably the reagent is a neutral and/or an alkaline reagent. A second matrix material can be obtained and added to the first matrix material after at least one cell is disposed in each of the plurality of cell assay locations. Either or both of the matrix materials can include one or more cell capture sites. In one embodiment, the cell capture sites are recesses formed in the matrix material. Further, a divider can be placed over the first matrix material and a second matrix material having a plurality of cells disposed therein can be placed above the divider. Any number of dividers and matrix materials can be used. In another embodiment, the plurality of cells can be printed onto one or more matrix materials.

The present disclosure makes it possible to perform multivariable analysis on a single sample, which makes it possible to reveal how fast an individual's cells repair different classes of DNA lesions. It also makes parallel processing of a multitude of samples at a time possible, which can assist in facilitating epidemiological studies of DNA repair among different individuals.

Further, the impact created by the present disclosure can be found in a variety of areas. With respect to the environment, the disclosures can allow for the assessment of baseline DNA damage levels in different populations, for instance by detecting environmental genotoxins prior to observable increases in disease prevalence, and the early detection of environmentally-induced genotixity can in turn give rise to population-wide intervention before significant problems arise. With respect to genes, the disclosures can allow genetic factors that modulate DNA damage levels to be identified, which can in turn assist in the discovery of genes that modulate genomic stability. With respect to gene-environment interactions, the disclosures can assist in the identification of individuals who have an increased susceptibility to DNA damage, which can then be used to help determine strategies for personal intervention. With respect to intervention itself, the disclosures can assist in assessing the effectiveness of different interventions by monitoring levels of DNA damage in individual or population-wide studies. For example, the disclosures can be used to assess the efficacy of dietary changes in patients with low DNA repair capacity. With respect to susceptibility markers, the disclosures can help assess inter-individual variation in the integrated ability of a person's cells to repair DNA damage, which in turn can reveal potential combinatorial effects of multiple subtle polymorphisms in repair genes. With respect to cell-type specific knowledge, specific cell types can be assessed for their DNA damage burden and repair capacity as a result of the disclosures, thereby permitting the assessment of the viability of targeting particular populations of cells. With respect to small sample requirements, the disclosures can reduce the number of cells needed for analysis, which results in less cells being used and makes the usage of such disclosures in epidemiological studies more useful.

BRIEF DESCRIPTION OF THE DRAWINGS

The invention will be more fully understood from the following detailed description taken in conjunction with the accompanying drawings, in which:

FIG. 1 is a perspective view of one exemplary embodiment of a self-contained assay cassette;

FIG. 3 is a schematic top view of a matrix material having an array of predetermined locations in a grid pattern;

FIG. 8A is a schematic, perspective view of a template for forming a matrix material having a plurality of cell assay locations, illustrating the introduction of a material for forming the matrix material to the template;

FIG. 8B is a schematic, perspective view of the resulting matrix material formed from the material of FIG. 8A having a plurality of cell assay locations;

FIG. 8C is a schematic, perspective view of the matrix material of FIG. 8B having a plurality of cells introduced to the matrix material;

FIG. 8D is a schematic, perspective view of the matrix material of FIG. 8B having cells disposed in the cell assay locations and excess cells removed;

FIG. 8E is a schematic, perspective view of the matrix material of FIG. 8B having a second matrix material formed on the first matrix material;

FIG. 9A is a schematic, perspective view of an agarose gel and a stamp for forming a matrix material;

FIG. 9B is a schematic, perspective view of the agarose gel and stamp of FIG. 9A with the stamp being positioned in the agarose gel;

FIG. 9C is a schematic, perspective view of a matrix material having a plurality of microwells that results from the solidification of the agarose gel of FIG. 9B with the stamp being removed;

FIG. 9D is a schematic, perspective view of the matrix material of FIG. 9C having a cell disposed in each of the plurality of microwells of the matrix material, and a close-up, side view of one row of the microwells having cells disposed therein;

FIG. 9E is a schematic, perspective view of the material matrix material of FIG. 9D having a second agarose gel solidified above the first matrix material to form a second matrix material, and a close-up, side view of one row of the microwells having cells disposed therein with the second matrix material disposed above;

DETAILED DESCRIPTION

Figure 2A:
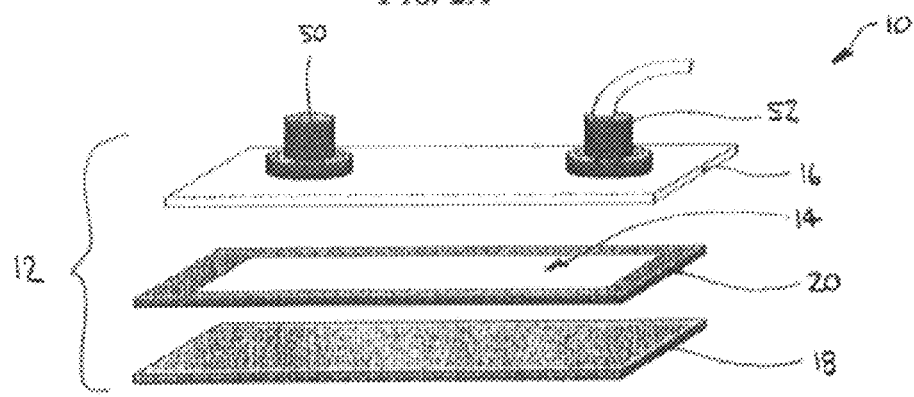
FIG. 2A is an exploded view of another embodiment of a self-contained assay cassette.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Devices, systems, and methods are generally provided for analyzing nucleic acid, such as DNA, for damage and repair. More particularly, the teachings discussed herein are aimed at creating efficient, consistent, and reliable devices, systems, and methods that are capable of analyzing nucleic acids for damage and repair at any cell cycle phase. The present invention can improve the standardization of such analyses that currently is lacking between laboratories, between individuals within a single laboratory, and even between assays and/or tests performed by the same individual. Further, the high throughput capabilities of the devices, systems, and methods discussed herein also allow for parallel processing, which can be used for simultaneous analysis of a large number of samples or conditions in a short time frame.

The term "cell" as used herein is intended to encompass any biological material derived from a cell, including but not limited to, living cells, cells that have been fixed, stained, lysed, or partially degraded, as well as cellular extracts or isolated nuclear components. The term "cell" can also include more than one cell, for instance when the "cell" can be a tissue sample. Tissue samples can be used with this invention in a number of capacities, for example in core biopsies where it can be advantageous to assess DNA damage and repair in tissue isolates. The term "matrix material" is used herein to describe any material capable of facilitating nucleic acid migration in the presence of an electromotive force, such as an applied electric current. Such matrix materials include but are not limited to agarose gels, polyacrylamides, and other polymeric materials. The terms "DNA" and "nucleic acid" are used interchangeably herein and should be read to encompass deoxyribonucleic acids, ribonucleic acids ("RNA"s), peptide nucleic acids, and the like, in native form, in chemically modified forms, or in fragments suitable for analysis. The terms "in" and "on" are used interchangeably herein. For example, a cell that is "in a matrix material" can be embedded, partially embedded, or located on the surface of the matrix material. Likewise, a cell "on a matrix material" can be situated on the surface of the matrix material or be partially or totally embedded therein.

One exemplary embodiment of a device for analyzing nucleic acids is illustrated in FIGS. 1 and 2A-2C. The device is a self-contained electrophoresis assay cassette 10 that is configured to receive one or more cells 100 for analysis. The cassette 10 generally includes a housing 12 that defines at least one inner cavity 14, a matrix material 30 that is disposed within the cavity 14, and an opening 50 to allow for the introduction of the one or more cells 100 into the cassette 10. The matrix material 30 can include one or more cell assay locations such that when the cells 100 are introduced into the cavity 14, the cells 100 can be distributed to at least some of the cell assay locations. In alternative embodiments, the device for analyzing nucleic acids can be a receptacle capable of receiving a matrix material that is configured to capture a plurality of cells on the matrix material. The matrix material can have multiple sites for such cell capture, such as recesses, and the receptacle itself can serve as a defined frame of reference for spatial differentiation of the matrix material.

Figure 2B:
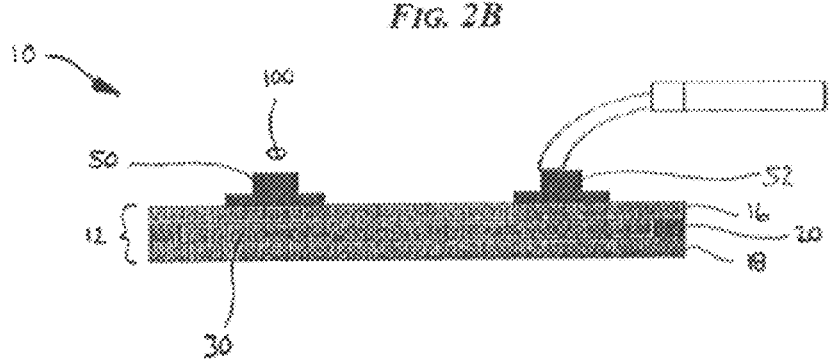
FIG. 2B is a side cross-section view of the self-contained assay cassette of FIG. 2A in a constructed form.
Figure 2C:
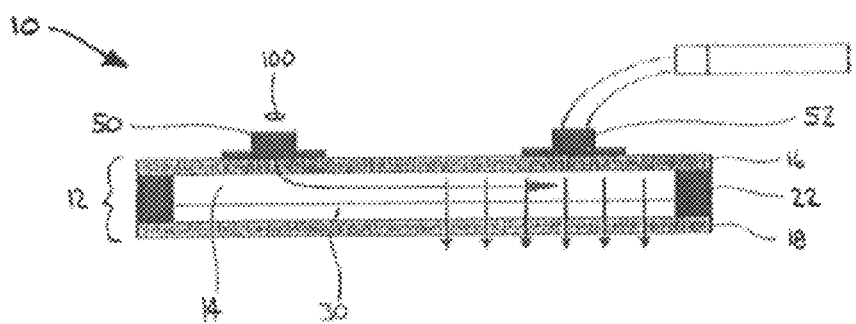
FIG. 2C is a side cross-section view of the self-contained assay cassette of FIG. 2A in a constructed form having a larger gasket and illustrating a fluid passing through the cassette.

The housing 12 of the cassette 10 can have a variety of shapes, but as illustrated it is substantially rectangular. It can be formed from a single material or from multiple materials, including but not limited to glass, plastic, and polymer materials. In one exemplary embodiment, the housing is formed by two transparent layers, for example top and bottom slides 16, 18, and has walls disposed between the two layers so that the cassette 10 is self-contained. The walls can be formed on their own or they can be part of a component disposed between the two layers. As shown in FIGS. 2A and 2B, the walls are formed by a gasket 20 disposed between the slides 16, 18. The gasket 20 includes an open space between the two walls that serves as the cavity 14. The gasket 20 can be made of a variety of materials, but in one embodiment it is elastic. Although in the illustrated embodiment one gasket 20 is shown, any number of gaskets can be used, depending on the desired height of the cassette 10. Furthermore, as will be described in further detail below, the gasket 20 can be configured to increase its height or even be replaceable such that a second gasket 22, as illustrated in FIG. 2C, can be substituted for the first gasket 20 to create a different height of the cassette 10.

Although the illustrated embodiment includes a gasket, the cassette does not need to include a gasket. In an alternative embodiment, a material for protecting the stability of the matrix material against tears, shreds, distortions, or other types of harm that can result from the flow of fluid across the matrix material is disposed above at least a portion of the matrix material. The protection of the matrix material can be achieved in a variety of manners, such as using a material like a membrane or a mesh, performing chemical modifications of the matrix material to make it more stable, or using other strategies that a person having ordinary skill in the art would recognize as capable of preventing shear forces from disrupting a matrix material. In another alternative embodiment, the cassette can include the matrix material disposed on a first surface and a fluid flow chamber disposed on a second surface, and the two surfaces can then be sandwiched together.

The cavity 14 can have a variety of shapes as well, but its shape can often be dictated by the shape of the housing 12. Accordingly, the shape of the cavity 14 in the illustrated embodiment is substantially rectangular. The cassette 10 can also include multiple cavities disposed therein, each of which can be configured for use like the cavity 14, or for other generally understood purposes. The cavity 14 is generally configured to receive one or more matrix materials, such as matrix material 30. A base of the cavity, which as illustrated is defined by the bottom slide 18, can be generally flat to allow for uniform distribution of the matrix material 30 within the cavity 14. In other embodiments, any number of shapes and figures can be formed in or on the base of the cavity to allow the matrix material to form in such any number of shapes and figures. The base of the cavity 14 can also be coated with a variety of materials and polymers that assist the base in having desired physical and/or biological attributes. One example of a desired physical attribute is improved adherence and/or stability capabilities such that the matrix material 30 more easily adheres to and/or is more stable with respect to the base of the cavity 14 when various buffers are run over its surface, as further described below. For example, when the matrix material 30 is an agarose gel, the coat can be an agarose pre-coat frosted on the bottom slide 18. In terms of biological attributes, the base of the cavity 14 can be modified with biologically active molecules such that different portions of the matrix material have varied microenvironments. Non-limiting examples of biologically active molecules include extracellular matrix materials, chemicals, biologicals, environmental toxins, and molecules designed to modulate cell behavior, such as short hairpin RNAs. In an exemplary embodiment, the bottom surface of the cassette 10 is coverslip thick glass so that cells can be analyzed at various times post exposure for their morphology, fluorescence, or even for characteristics that can be revealed through immunohistochemistry.

An opening 50 to allow the introduction of cells into the cassette 10 can be located in any number of locations on the cassette 10, and any number of openings can be included in the cassette 10, although it is generally preferred to limit the number of openings so that a substantially uniform environment within the cassette 10 can be maintained. As illustrated, the opening 50 is located on the top slide 16 and is in communication with the cavity 14 such that when the cells 100 are introduced into the opening 50 they move through the opening 50 and into the cavity 14. When a matrix material 30 is disposed in the cavity 10, the cells 100 can interact with the matrix material 30. For example, the cells 100 can be distributed to any number of cell assay locations formed in or on the matrix material 14. One or more cells 100 can be located at a single cell assay location. When the top layer of the cassette 10 is transparent, it is preferable that the opening 50 be located on a side of the cassette as opposed to the top so that the view inside of the cassette 10 is not obstructed by the opening 50. In an alternative embodiment, the housing includes a removable portion through which cells can be introduced into the cavity. For example, a portion of a top layer, or the entire top layer itself, can be configured to open and close, or alternatively, a portion of a top layer, or the entire top layer itself, can be removable to allow entry of the cells into the cavity and then the top layer can be returned back to its original position.

The size of the cassette can vary with the intended uses, but it is generally sized for use in a laboratory with a standard gel electrophoresis apparatus and an epifluorescent microscope. While the length, width, and height of the cassette have no real minimum or maximum measurement limitations, generally the length l of the cassette 10 can be in the range of approximately 100 millimeters to 100 centimeters and preferably is approximately 7.5 centimeters, the width w in the range of approximately 1 millimeter to 100 centimeters and preferably is approximately 2.5 centimeters, and the height h in the range of approximately 0.01 millimeters to 10 centimeters and preferably is approximately 0.5 millimeters. In the illustrated embodiment of FIGS. 2A and 2B, the slides 16, 18 and the gasket 20 are approximately each 100 microns thick, and the second gasket 22 of FIG. 2C is approximately 500 microns thick, but generally the thickness of the slides 16, 18 can be in the range of approximately 20 micrometers to 3 millimeters and the thickness of any gasket disposed therebetween can be in the range of approximately 20 micrometers to 10 centimeters. However, similar to the length, width, and height of the cassette, the dimensions of any slides or gaskets have no real minimum or maximum measurement limitations and such dimensions are generally selected based on the intended use of the component.

A matrix material 30 can be disposed in at least a portion of the cavity 14 defined by the housing 12 and is generally configured to facilitate nucleic acid migration in response to electrophoresis. As will be explained in further detail below, disposal of the matrix material 30 in at least a portion of the cavity 14 can occur by first solidifying the matrix material 30 and then disposing it in the cavity 14 or the matrix material 30 can enter the cavity 14 and then be solidified. In an exemplary embodiment, the matrix material 30 is located on a base portion of the cavity 14. In the illustrated embodiment, the matrix material 30 is disposed on the bottom slide 18. Although the matrix material 30 can be made of many different substances, in preferred embodiments the matrix material 30 is substantially gel-like. In one exemplary embodiment the matrix material 30 is made of an agarose gel. An agarose gel is particularly useful because the temperature at which it solidifies, the importance of which is described in more detail below, is much lower than the temperature required to re-melt the agarose. For example, a one percent solution of Ultra Low Melting Agarose produced by the USB Corporation gels at approximately 46 to 61 degrees Fahrenheit, but does not re-melt until approximately 145 degrees Fahrenheit. Accordingly, when cells are distributed to cell assay locations of the matrix material 30 and solidified in a desired location, the solidified matrix material 30 will not re-melt if a molten agarose is placed near the original matrix material 30 to create a second matrix material. The ability to use agarose gel to form a matrix material was surprising because a person skilled in the art would generally expect such a material to tear when trying to mold it into desired configurations, including the types of configurations discussed in greater detail below. Further, a person skilled in the art would not generally expect useful and accurate comets to result from cells disposed in an agarose gel of the types described. The matrix material 30 can be made of multiple substances, but it is generally preferred to use a single substance because minimizing the number of variables affecting the results is advantageous and the use of a uniform, single substance generally provides for less possibility of variations that could affect the outcome between assays.

The matrix material 30 can include one or more cell assay locations. The cell assay locations can be in any number of locations in or on the matrix material 30. As will be explained in further detail below, cells can be associated with the matrix material prior to solidifying the matrix material, for instance by mixing the cells with the matrix material and then disposing the mixture in the cavity 14 of the cassette 10, or after solidifying the matrix material, for instance when arrays are first created in the matrix material 30, such as by forming microwells, and then the cells are introduced. Further, a combination of both of these methods can be used. In some embodiments, the locations are predetermined be design, while in other embodiments the locations results from adding cells to the matrix material and the cells becoming distributed to various locations in the matrix material. In an exemplary embodiment the cell assay locations are disposed on a proximal surface of the matrix material 30, thereby allowing the cells that engage with the cell assay locations to be located on or near the surface of the matrix material. Locating the cells closer to the surface can increase the speed of the assay. When the locations are not predetermined, a thickness of the matrix material 30 can be kept relatively small and uniform such that cells that arrive at cell assay locations generally have a uniform depth within the matrix material 30. In one embodiment the thickness of the matrix material 30 can be in the range of approximately 10 to 300 microns, and preferably is approximately 100 microns. Any number of devices can be used to create a matrix material having a uniform thickness. In one exemplary embodiment, the cassette 10 is configured to create a matrix material having a uniform thickness, which is discussed in further detail below.

In embodiments in which microwells are used to form the cell assay locations, the depth of the microwells can be selected to optimize various parameters, such as the number of cells disposed in each microwell. For example, in one embodiment microwells having depths of approximately 10, 12, 14, 16, 18, and 20 micrometers can be formed in a matrix material, and the microwells having larger depths can generally retain more cells. In an embodiment in which the cells are TK6 lymphoblastoid cells, a 10 micrometer microwell can retain a single cell (although in some instances two cells can be retained), while a 20 micrometer microwell can retain approximately as many as seven cells. Because different cells have different sizes, each microwell can be sized to accommodate a desired number of a particular type of cell. Accordingly, a matrix material can be configured to have particular microwell sizes to retain particular types and numbers of cells on the matrix material. Surprisingly, when multiple cells are disposed in a single microwell, a larger, but normal comet can be produced. Multiple cells in a single microwell, however, can sometimes lead to asymmetrical morphologies, which are not typically useful for analyses because they can be more difficult to analyze.

The depth of microwells can be uniform in a particular matrix material, or one matrix material can include microwells having a variety of depths. Furthermore, although well sizes ranging between 10 and 20 micrometers are discussed in one embodiment, a variety of other well sizes can be used. Some microwells can be smaller, such as, by way of non-limiting example, 8, 6, or 4 micrometers, while some can be larger, such as, by way of non-limiting example, 30, 50, or 80 micrometers. However, as microwell depth size increases, the ability of the DNA to sufficiently separate from the well decreases, which in turn can affect the consistency and accuracy of the tests. In one exemplary embodiment, the microwells have a depth in the range of approximately 12 to 30 micrometers, and preferably in the range of approximately 12 to 20 micrometers.

When the cell assay locations are predetermined, the cell assay locations can be arranged in any number of shapes and designs. The type of arrays used for the cell assay locations will vary depending on the intended use, such as the types of tests that will be run and the types of results that will be analyzed. The formation of the arrays will be discussed in more detail below, but generally the arrays can include one or more cell capture sites configured for receiving cells. The sites can be any shape or size, for instance, by way of non-limiting examples, recesses, wells or troughs. Alternatively, the cell assay locations can include harbor high affinity molecules that capture specific cell types, such as circulating tumor cells. More specifically, cells can be captured and arrayed using antibodies or other molecules that bind with high affinity to specific cell types. Capturing a plurality of cells on a single matrix material allows for multiple results to be achieved in a single test. Thus, for example, by placing 40 cell capture sites on a single matrix material, a single matrix material can replace 40 traditional comet slides and a single test can replace 40 tests. Likewise, if three matrix materials, each having 40 cell capture sites, are coupled together, as discussed in further detail below, three matrix materials can replace 120 traditional comet slides and a single test can replace 120 tests.

In one exemplary embodiment, illustrated by FIG. 3, the array can be a grid 132 where the location and spacing of the cells 100 distributed to the cell assay locations is known and generally consistent between matrix materials, such as matrix material 130. Furthermore, as shown in FIG. 3, the cassette 10A can include electrodes 131 and 133 to apply a current across the matrix material 130. Any number of electrodes can be included in a cassette, and the electrodes can be disposed in any portion of the cassette. By setting up such an array, hundreds of samples can be processed in a consistent fashion in parallel such that each array has a nearly identical local environment. Further, the results will be much more reliable, able to be reproduced, and produced much quicker, i.e. the throughput will be greatly enhanced because the array allows for multiple samples to be run and for the locations of those samples to be known and consistent. This, in turn, results in a reduction of noise due to inhomogeneities of the cellular microenvironments that can occur when many tests are run. For example, a substantially consistent z plane for each cell can be achieved and the x and y coordinates for each cell can also be known and/or predetermined. Still further, matrix materials can be formed in a manner that allows cells in one region to be fixed while simultaneously enabling other regions to repair.

The cells used in the cassette 10, or the matrix material 30 in general, can be any kind or type of cell from any living organism. Some cell types include ovarian carcinoma, primary rat hepatocytes, and lymphocytes. Surprisingly, not only can many types of cells be used in the systems and devices described herein and still survive over an extended period time of at least several days, but the cells can even proliferate in the matrix material 30. In one exemplary embodiment the cells can be taken from a human. For example, the cells can be nasal epithelial cells or buccal cells taken from the inside of a cheek. In a preferred embodiment, white blood cells are particularly useful for research purposes because they are often collected and stored in large scale epidemiological studies. In fact, previous types of comet assays have already been proven to be effective using white blood cells for detecting differences in the levels of DNA damage among populations of people exposed to different conditions (e.g., Andreoli et al. 1997, Piperakis et al. 2000; Cebulska-Wasilewska et al. 2005; Bhalli et al. 2006; Botta et al. 2006.) Furthermore, several studies have shown that people who carry genetic deficiencies in DNA repair can be identified when repair kinetics are measured using a comet assay on their white blood cells (e.g., Alapetite et al. 1996; Collins et al. 2001; Burger et al. 2006.)

In addition to the cassette 10 and the matrix material 30 being able to handle a number of different cell types, the cassette 10 and the matrix material 30 can be configured to handle a number of different cell types on the same cassette 10 or matrix material 30. For example, different cell capture sites or microwells can be configured to hold particular cell types, or alternatively, a single cell capture site or microwell can be configured to hold more than one cell type. This allows for multiplexing of cell types and chemicals in order to conduct high throughput screens, for example for drug screening and epidemiological inquiry. In one embodiment fluorescent labeling can be used to assist in visually differentiating randomly seeded cell types. Labeling, in conjunction with spatial encoding to allow for an "address" to be created for each cell and/or well, can allow for the evaluation of the identity of each cell prior to conducting a comet assay. After analysis, the two data sets can be merged to delineate the responses of specific subpopulations.

In one exemplary embodiment, red, green, and blue Celltracker dyes (manufactured by Molecular Probes) can be used to multiplex three cell types. The cells can be imaged before experimentation in case a lysis step disrupts any cell membranes that results in the loss of the Celltracker dye(s). A chart illustrating the location of each cell can then be created, for example by using a macro-script for a fluorescent microscope to provide Cartesian coordinate registration with respect to cell color of each of the cells. The results can then be analyzed, relying in part on the chart to determine the results with respect to each cell. By color-coding the cell types, the cells can be mixed together, even within a particular macrowell or microwell, and still yield useful results.

One exemplary way of creating a matrix material that is particularly compatible with living cells is to prepare a matrix material with media in place of buffer. In such an embodiment, single cell types, mixtures of cells, or tissue samples can be embedded in the matrix material and maintained under conditions that modulate cell behavior. In fact, tissue samples can even be analyzed for DNA damage levels when frozen. Multiple samples can be taken from a tumor to assess DNA damage/repair at different positions, for instance central versus peripheral. This can in turn allow studies of the extent to which chemotherapeutics penetrate a tumor. For example, levels of cisplatin adducts present in DNA can be evaluated by adding DNA damage-specific endonucleases, such as UVRabc. Being able to analyze samples of tissues, as opposed to disaggregate cells, can also assist in overcoming the problem of DNA damage that increases as a result of the stresses involved in tissue disaggregation to produce the cells for analyzing. In addition to being able to modulate cell behavior, normal cell behavior can also be facilitated by mixing the matrix material with materials that facilitate such behavior, or by chemically modifying the matrix material to facilitate normal cell behavior. For example, various chemicals and biologicals can be printed onto the matrix material to create various microenvironments that affect cell behavior and/or differentiation. Still other types of cell conditions could also be emulated for various types of analyses. By way of non-limiting example, hypoxic conditions like those found in a tumor can be emulated so that in vitro conditions can more closely mimic the conditions of cells or tissues in vivo.

In some embodiments live cells can be stained in situ within the matrix material and can remain so for extended periods of time. This can allow for the identification of cell types, as well as particular states within the cells themselves, such as annexin V for apoptosis. Responses, such as phosphorylation patterns, can also be identified and the various end points of the live cells can be combined with the disclosed assay to get an integrated biological readout of many end points on the same platform. Alternatively, the cells can be added to the matrix material by way of a robotic system. In one exemplary embodiment the robotic system can transfer volumes of media containing cells onto a matrix material by way of a liquid transfer such that many different cell samples can be processed in parallel.

As discussed above, the location of the cell assay locations can be predetermined in some sort of an array, such as a grid. In a preferred embodiment, the cell assay locations are predetermined and consistent between tests, users, and laboratories where such uniformity would prove beneficial. For example, a particular protocol for manual creation of the cell assay locations can be used. One type of device for such manual creation of cell assay locations is a multipipettor. A multipipettor can be applied to a matrix material to create a plurality of cell capture sites, in this instance defined by wells. More particularly, multipipettors are typically optimized for moving liquid in 96 well plates, and thus can create a plurality of uniform wells adapted for receiving droplets of cells and/or testing agents, which will be discussed in further detail below. An alternative way of manually creating an array is to use a plurality of bolts or pins that are organized in a desired pattern. The size of the bolts or pins, as well as the desired pattern, can easily be changed to allow for any number of arrays with any number of cell capture site sizes. A bracket system can be used to hold the bolts or pins in a desired pattern for easy substitution of the bolts or pins and maintenance of the desired pattern. Alternatively, automated devices can be used to produce such uniform cell assay locations between matrix materials. Many elegant robotic devices have been developed to facilitate liquid handling for genomics. For example, a "SpotBot," a robotic device that robotically controls pin movements to transfer liquids from 96 well plates to glass surfaces, can be used. The principles are identical to the bolt or pin method described above. Accordingly, any combination of manual or automated methods can be used to create cell capture sites such as troughs, wells, or recesses.

Figure 4:
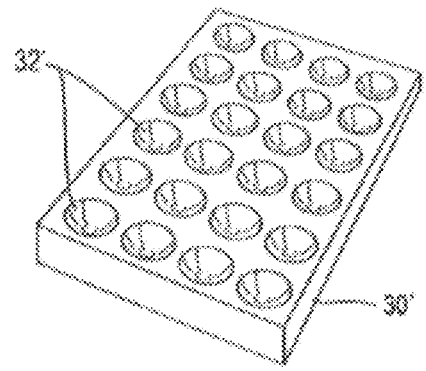
FIG. 4 is a perspective view of one exemplary embodiment of a matrix material having an array of macrowells.
Figure 5:
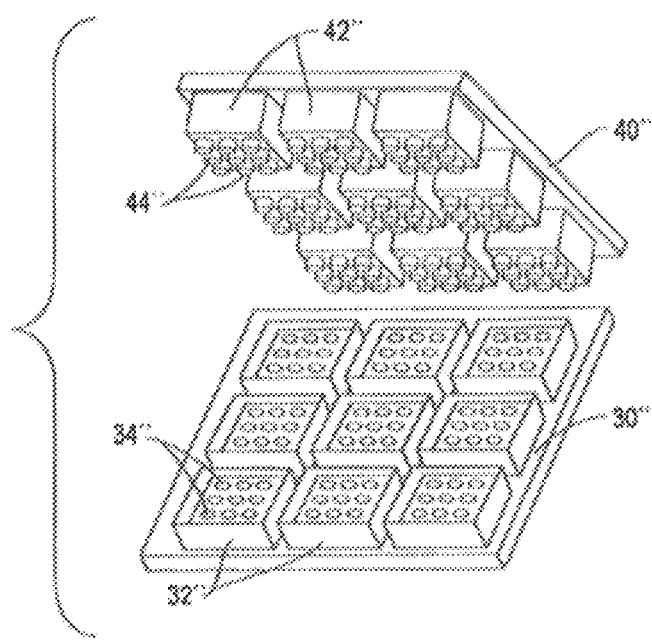
FIG. 5 is schematic perspective view of another exemplary embodiment of a matrix material having an array of macrowells and microwells and a template to assist in forming the same.

While matrix materials can be configured in a variety of different ways to optimize the number of cells and conditions to be analyzed, in an exemplary embodiment illustrated in FIG. 4, a matrix material 30' includes a plurality of macrowells 32' configured to receive one or more cells. Further, the macrowells 32' can include a plurality of microwells (not shown) configured to receive one or more cells. In the illustrated embodiment the matrix material 30' includes 24 macrowells 32'. In one exemplary embodiment each macrowell 32' includes a 50 by 50 microwell array, thus including 2500 microwells on the matrix material 30'. In another exemplary embodiment of a matrix material, illustrated in FIG. 5, a matrix material 30" includes a plurality of macrowells 32", which in turn include a plurality of microwells 34". While the illustrated embodiment includes 9 macrowells 32", each including a 3×3 array of microwells 34" for a total of 81 microwells, any number of macrowells 32" and microwells 34" can be used, including non-uniform amounts of microwells 34" formed in different macrowells 32". For example, 100 microwells can be located in one macrowell while 50 microwells can be located in an adjacent macrowell. Likewise, while the embodiments illustrated in FIGS. 4 and 5 include 24 and 9 macrowells, respectively, in other embodiments more or less macrowells can be formed, for example 96 or 384 macrowells. As also shown in FIG. 5, the macrowells 32" and microwells 34" can be formed by way of a template 40" having macro-protrusions 42" and micro-protrusions 44" to assist in forming the macrowells 32" and microwells 34", respectively.

Figure 6A:
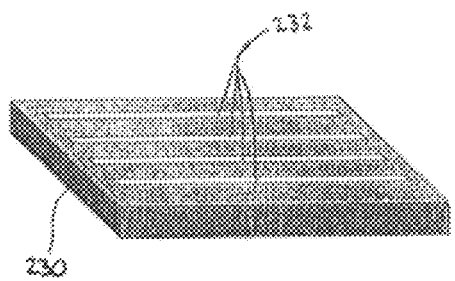
FIG. 6A is a perspective view of a matrix material having a plurality of troughs disposed therein.
Figure 6B:
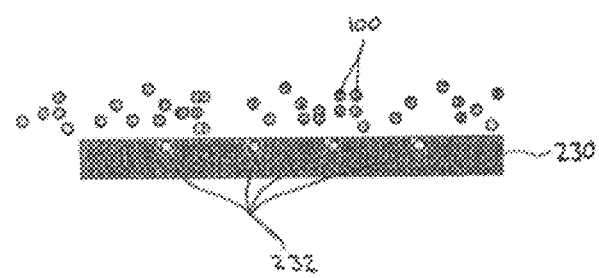
FIG. 6B is a side view of the matrix material of FIG. 6A, illustrating the introduction of a plurality of cells to the matrix material.
Figure 6C:
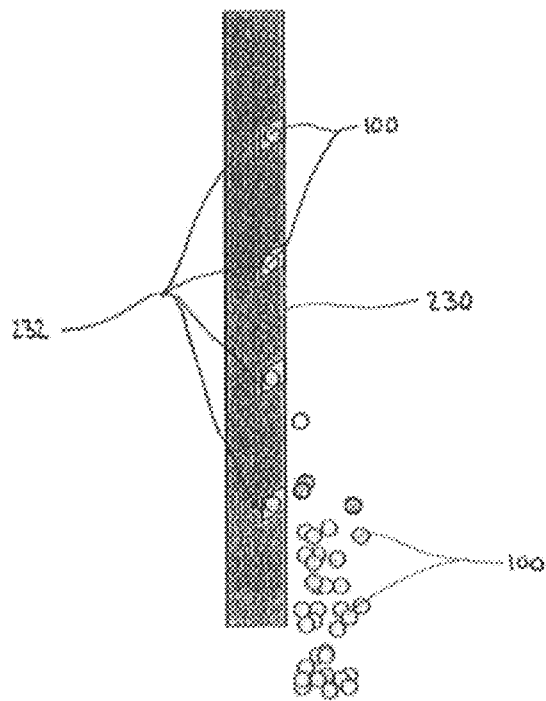
FIG. 6C is a side view of the matrix material of FIG. 6A, illustrating the matrix material rotated 90 degrees to remove excess cells from the matrix material.

Once cell assay locations, such as cell capture sites, have been created, there are a number of different methods that can be used to distribute the cells to cell assay locations. In one embodiment illustrated in FIGS. 6A-6C, the cell assay locations are a plurality of troughs 232 disposed in a matrix material 230. In an exemplary embodiment, as best illustrated in FIGS. 6B and 6C, the troughs 232 are angled. Cells 100 can be introduced to the matrix material 230 such that one or more cells 100 are distributed into the troughs 232. Once a desired number of cells 100 are located in the troughs 232, the excess cells 100 can be removed in any number of manners, but in the illustrated embodiment they are removed by rotating the matrix material 230 at a 90 degree angle such that the cells 100 not located in the troughs 232 drop off the matrix material 230, leaving only the cells 100 in the troughs 232 for use in the analysis. Alternatively, one or more aspirators can be used to aspirate away particular cells under particular conditions.

Figure 7A:
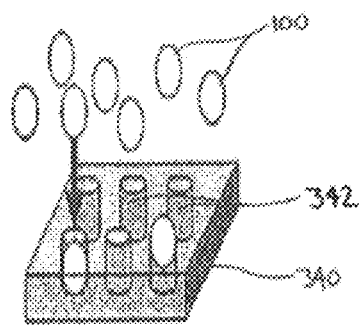
FIG. 7A is a schematic, perspective view of a template for receiving a plurality of cells.
Figure 7B:
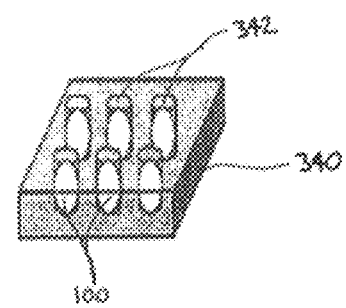
FIG. 7B is a schematic, perspective view of the template of FIG. 7A having cells disposed therein and excess cells removed.
Figure 7C:
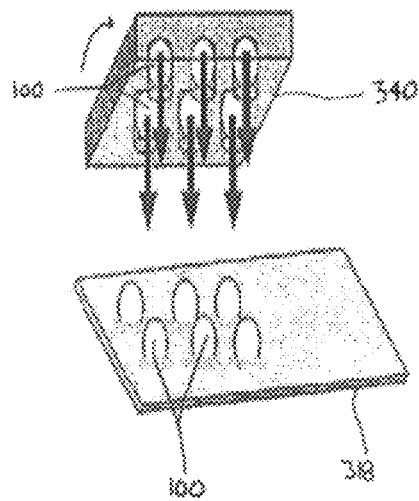
FIG. 7C is a schematic, perspective view of the template of FIG. 7A, rotated 180 degrees, and a base of a self-contained assay cassette.
Figure 7D:
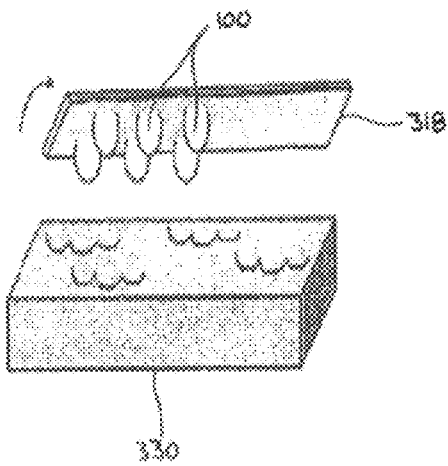
FIG. 7D is a schematic, perspective view of the base of a self-contained assay cassette of FIG. 7C, rotated 180 degrees, and a matrix material.

Another embodiment of a method that can be used to distribute cells to cell assay locations is illustrated in FIGS. 7A-7D. FIG. 7A illustrates a mold or template 340 having one or more pits or wells 342 for receiving cells 100. Cells 100 can be introduced to the template 340 such that one or more cells 100 are distributed into the one or more wells 342. Gravitational forces alone should be sufficient to allow the cells 100 to be distributed into the wells 342, but other mechanisms can be used to assist the cells 100 into the wells 342. Once a desired number of cells 100 are located in the wells 342, the excess cells 100 can be removed in any number of manners, for instance by wiping the excess cells 100 away from the surface or running a liquid horizontally across the surface, leaving the template 340 having the desired number of cells 100 disposed therein as illustrated in FIG. 7B. (Chin et al. 2004.) A slide 318 for use as a base of a cassette is provided and the one or more cells 100 located in the template 340 can be evacuated from the template 340 by any number of manners. In the illustrated embodiment of FIG. 7C, the template 340 is rotated 180 degrees to allow the cells 100 to fall out of the template 340 and onto the slide 318. In an exemplary embodiment the slide 318 is pre-coated with poly-L-lysine to assist in adhering the array of cells 100 to the slide 318. Once the cells 100 are associated with the slide 318, a matrix material 330 is introduced to assist with solidifying the location of the cells 100. In the illustrated embodiment the slide 318 and associated cells 100 are rotated 180 degrees to be engaged with the matrix material 330. Alternatively, the matrix material 300 can be added directly onto the slide 318 without any rotation of the slide 318 and/or the cells 100.

Another approach that can be used for cell patterning is dielectrophoresis. One way of carrying this process out is by sandwiching cells between two conductive glass slides. In a preferred embodiment the slides are pre-coated with indium tin oxide. A thin layer of insulating material can also be photomasked onto the bottom slide to form electrodes in the remaining unmasked areas. An alternating current can be applied across the top and bottom surfaces to achieve a non-uniform electric field, which in turn causes cells to cluster within approximately one to three minutes. After the cells are put into desired cell assay locations, ultraviolet light can be used to crosslink the polymer and hold the cells in position. (Albrecht et al. 2006.) In a preferred embodiment, the cells can be suspended in a matrix material and positioned in a single cell array using this method, and then the matrix material can be chilled to solidify the matrix material and thus the cell locations. Adjustments of the cell concentration allow the spacing between the cells in the array to be substantially uniform.

Alternatively, printing methods can be used to associate the cells and the matrix material. In one embodiment the cells can be printed directly onto the matrix material or onto a surface that can be adhered to the matrix material. In another embodiment the cells can be printed onto a solid surface and be subsequently submerged into a molten gel, such as low melting temperature agarose, to then be solidified into desired locations. One way in which the cells can be arranged into desired locations is based on each cell's ability to bind to a pattern of molecules that are arranged on the solid surface.

Using the methods taught herein, as well as a number of other methods that can also be used to create cell arrays, allows for thousands of cells to be patterned in an array, such as a grid, in and/or on a matrix material. By placing multiple samples on a single matrix material, result variation from matrix material-to-matrix material can be significantly reduced. Further, the methods described herein can be altered in a variety of ways. For example, in the embodiment illustrated in FIGS. 6A-6C, the matrix material 230 could be a template similar to the template 340 of FIGS. 7A-7D such that the cells 100 in the troughs 232 are distributed to a separate matrix material. Similarly, the steps of using a template and/or a slide as discussed with respect to FIGS. 7A-7D can be eliminated such that the cells 100 are distributed directly to a matrix material, similar to the methods described with respect to FIGS. 6A-6C. Further, the method described with respect to FIGS. 7A-7D can be altered such that rather than evacuating the cells 100 from the template 340 onto a slide 318, instead the cells 100 can be evacuated to a cavity of a cassette and then a matrix material can be added. A person having ordinary skill in the art would recognize the many variations of these two methods, as well as a plethora of other methods, can be used to create arrays in matrix materials. The number of cell assay locations within a particular matrix material, and the patterns and designs of the arrays, can be essentially limitless.

Further, just as a variety of methods can be used to create cell arrays in a matrix material, a number of methods can be used to create a matrix material having one or more cell assay locations. For example, photolithographic molds or templates, sometimes referred to as masks or stamps, can be used to help create approximately uniform matrix materials having microwells of approximately uniform dimensions. Protrusions formed as part of the molds or templates can form the microwells. The masks can crosslink photoresist onto silicon wafers. In one exemplary embodiment of a mold or template, protrusions of the template have a pitch of approximately 200 micrometers, a depth of approximately 50 micrometers, and diameters in the range of approximately 10 to 30 micrometers. The template and resulting matrix material can have any number of desired dimensions and shape, based at least, in part, on the desired use and desired design. Using a mold or template to form matrix materials can allow for the formation of multiple matrix materials that have similar dimensions. Thus, matrix materials need not be reused in order to create uniform conditions.

One method for creating a matrix material is illustrated in FIGS. 8A-8E. As shown in FIG. 8A, a mold or template 440 is provided having one or more features that are configured to create cell assay locations. In the illustrated embodiment, the features are protrusions 442 around which a liquid, such as molten agarose 434, will be solidified to form a matrix material 430. The molten agarose 434 is placed on the template 440 and forms around the protrusions 442 such that, once solidified, the areas occupied by the protrusions 442 are wells 432, shown in FIG. 8B. The resulting matrix material 430 can then optionally be placed on a base 418 that can be used as the base of a self-contained electrophoresis assay cassette.

As shown in FIG. 8C, cells 100 can be introduced to the matrix material 430 such that at least one of the cells 100 is distributed to at least one of the cell assay locations, e.g., the wells 432, and the cells 100 are subsequently incubated. The cells can be incubated in a number of different manners, but in one embodiment buffers are introduced to the cells to perform desired actions, such as cell lysis, staining with antibodies, endonucleolytic cleavage of the nucleic acid at specific types of lesions, nucleic acid denaturation, and/or electrophoresis.

Once the desired number of cells 100 are incubated in the desired number of cell assay locations, the excess cells 100 can be removed by any number of means, as shown in FIG. 8D.

Optionally, as illustrated in FIG. 8E, once the matrix material 430 is solidified and the cells 100 are located in the cell assay locations, a second matrix material 470 can be added to the matrix material 430 and solidified in a like manner. Alternatively, the initial matrix material 430 can be stained. This second matrix material 470 or staining can provide further stability to hold the cells 100 in the cell assay locations. By assuring a substantially uniform matrix material thickness, and by positioning cells 100 uniformly within the matrix material 430, a significant reduction in the amount of differences in the microenvironment that cells 100 experience during nucleic acid analysis can be achieved. Further, with respect to the template 440 of FIG. 8A, a person skilled in the art will recognize that in other embodiments the template 440 can have features such as inclusions rather than protrusions such that the liquid to be solidified into a matrix material forms cell capture sites by contouring around the template and then removing the template once the matrix material is solidified to reveal similarly shaped cell capture sites in the solidified matrix material.

Overall, any of the resulting arrays greatly enhance the reproducibility and speed of analysis. Arraying cells within a matrix material reveals the extent to which inhomogeneities in cellular microenvironments affect the assay. It also allows for high-throughput analysis of cells. By combining these two techniques, significant improvements in the analysis of nucleic acid damage and repair can be achieved. The subsequent results can then be useful in a wide variety of areas, but notably can be used to measure the levels of DNA damage in cells and the repair kinetics following a cell's exposure. A further benefit that results from the arrays is that one microwell, which can contain one or more cells, is in very close proximity to another microwell, which can also can contain one or more cells. By placing microwells in very close proximity to one another and/or by placing multiple cells within each microwell, the total surface area required per sample can be significantly reduced compared to the standard assay, which in turn facilitates multiplexing of varied samples and/or conditions, which is further discussed below.

One example of a method for forming a matrix material and seeding the material with cells is illustrated in FIGS. 9A-9E. As shown in FIG. 9A, a molten agarose gel 834 having a standard melting point can be poured onto a sheet of Lonza Gelbond 818 (manufactured by Fisher Scientific). A stamp 840 having protrusions 842, as also shown in FIG. 9A, can then be positioned in the agarose gel 834 and the gel 834 can be allowed to solidify at room temperature, as shown in FIG. 9B. As the agarose gel 834 solidifies, or once it is solidified, the stamp 840 can be removed from the gel 834, as shown in FIG. 9C. The stamp 840 can be removed from the agarose gel 834 using a number of different devices and techniques, for instance, by using forceps. Phosphate buffer saline can be added to the agarose gel 834 prior to removing the stamp 840 from the gel 834 to help minimize surface shear caused by removal of the stamp 840. The matrix material 830 that results from solidification of the agarose gel 834 includes microwells 832 formed by the protrusions 842 of the stamp 840. The matrix material 830 can, optionally, be sterilized, for example by using ultraviolet exposure. As shown in FIG. 8D, cells 100 can be seeded on the matrix material 830. In one embodiment a concentration of $2 \times 10^6$ cells/ml is allowed to settle into the microwells 832 of the matrix material 830 for approximately an hour before excess cells 100 are removed. A number of removal techniques can be used, including those discussed herein, but in this particular embodiment the cells 100 are removed by aspiration. Optionally, as shown in FIG. 9E, a second agarose gel can be overlaid over the matrix material 830 and can be allowed to solidify to form a second matrix material 870. The second agarose gel can have a low melting point (such as 37° C.) to help limit or prevent the cells 100 from escaping. In one exemplary embodiment, solidification of the second agarose gel can occur at 4° C. The resulting configuration can then be incubated in media overnight, which can allow the cells 100 to recover from any stress endured during handling. Methods for analyzing the cells 100 can then be performed, some of which are discussed herein.

Figure 10:
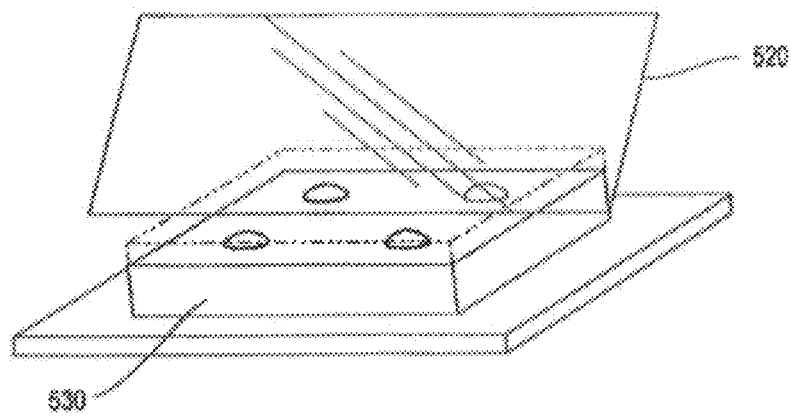
FIG. 10 is a perspective view of a matrix material having a plurality of cells disposed therein and a divider for placement on top of the matrix material.

In some embodiments, a plurality of matrix materials can be layered on top of each other to further expand the capabilities of the described methods, devices, and systems to allow even more analyses to occur in a single cassette. More particularly, layering matrix materials at least partially on top of each other increases the number of assays that can be run at one time regardless of whether a cassette is used. Each matrix material can include cell assay locations, and by layering the matrix materials the speed and types of analyses that can be performed are enhanced. In one embodiment, illustrated in FIG. 10, a divider 520 can be placed on top of a matrix material 530 that has cells 100 distributed to cell assay locations of the matrix material 530. The divider 520 can assist in at least partially stacking additional matrix materials on top of the first matrix material 530, although disposing a divider between matrix materials is optional. The divider 530 can be made of any number of materials, and can have any shape or size depending on the desired use and the number of subsections desired in the resulting apparatus. The surface area designated by the dividers can be large enough to encompass sufficient space for cells within one unit area to be analyzable following electrophoresis. In an exemplary embodiment the divider 530 is made from material that prevents cells 100 from moving from one section of the matrix material 530 to another section of the matrix material 530 or to another matrix material entirely. By way of non-limiting examples, such a material includes polypropylene or any other plastic material, solid, or mesh material. In a further exemplary embodiment, the divider 530 is substantially rectangular in shape, and has a length in the range of approximately 100 millimeters to 100 centimeters, a width in the range of approximately 1 millimeter to 100 centimeters, and a thickness in the range of approximately 0.01 millimeters to 10 millimeters. Further, in lieu of, or in addition to having a plurality of matrix materials, multiple layers can be disposed in a single matrix material.

Turning attention back to the cassette 10 as a whole, the cassette 10 can be constructed in any number of ways, but in the illustrated embodiment of FIGS. 2A-2C the gasket 20 is disposed between the top and bottom slides 16, 18. As seen particularly in FIG. 2B, the matrix material 30 is disposed in the cavity 14 formed by the gasket 20 such that it is sandwiched between the two slides 16, 18. Although the matrix material 30 does not need to fill the entire cavity 14, when the desire is to create a matrix material 30 having a substantially uniform thickness it can be advantageous to fill the entire cavity 14 such that the thickness is substantially uniform between parallel slides 16, 18. The introduction of the matrix material 30 into the cavity 14, as well as the cells 100, can be accomplished in any number of manners, but in one embodiment they enter by way of the opening 50. The order in which they enter is generally not important, for example the matrix material 30 can be introduced first and then the cells 100 can be added, or alternatively they can both be mixed together prior to introducing both into the cavity 14. Once both the matrix material 30 and the cells 100 are disposed in the cavity 14, the cassette 10 can be briefly chilled to allow the matrix material 30 to solidify and the cells 100 to solidify their locations within and/or on the matrix material 30. In one embodiment the cassette can be chilled at approximately 39 degrees Fahrenheit for approximately 30 minutes. In an embodiment where an opening to access the cavity 14 is large enough to accept a solidified matrix material, for instance when a top portion of the housing 12 is removable, the matrix material 30 and cells 100 can be solidified prior to introducing either into the cavity 14.

In some embodiments the cassette 10 can also include a fluid delivery system configured to introduce one or more reagents or buffers into the cassette 10. In the embodiment illustrated in FIGS. 1 and 2A-2C, the opening 50 can be used as a fluid delivery inlet port, and a second opening 52 can be used as a fluid delivery outlet port. Generally, the inlet port is configured to receive a fluid into the cavity 14 and the outlet port is configured to remove a fluid from the cavity 14. In the illustrated embodiment the outlet port is configured to exert a negative-pressure to suction the fluid out of the cavity 14, although a person skilled in the art would recognize a number of other techniques that can be used to remove the fluid from the cavity 14. Further, although it is preferred that the fluid that is introduced into the cavity 14 is removed from the cavity 14, it does not have to be removed. Removal of the fluid tends to lead to more accurate results though as the fluid can affect the substantially uniform nature of the self-contained electrophoresis assay cassette 10. However, as discussed in further detail below, in some embodiments it can be desirable for the fluid to remain in the cassette 10 and/or become part of the matrix material 30. Any number of fluids can be delivered to the cavity 14.

In one exemplary embodiment, a fluid that both promotes lysis and unwinds the nucleic acid is used. Alternatively, separate fluids for lysing and unwinding can be used. Generally, the fluid for promoting lysis is a neutral buffer while the fluid that unwinds the nucleic acid is an alkaline buffer. Various types of detergents, such as triton X100, sodium lauryl sarcosinate, and sarkosyl, can be effective to promote lysis of the cells. By varying the pH of the fluid applied to the cells being analyzed, it is possible to tune the assay to be differentially sensitive to different classes of DNA lesions. For example, a neutral comet assay can be more effective to reflect the levels of double strand breaks, while an alkaline comet assay can be more effective to detect single strand breaks and alkali sensitive sites. Alkaline conditions generally provide greater sensitivity to environmental conditions.

In the interest of standardization, however, it is generally preferred that the amount of detergents or other fluids that are use in the self-contained electrophoresis cassette 10 be standardized, either through procedures or automation, across similar assays. For example, currently the amount of detergent used ranges from about one-half to two percent, resulting in broadly differing concentrations for any one test. By standardizing the amount and type of reagents used, the results from various tests across laboratories or tests within the same laboratories can be greatly improved. Other fluids can also be introduced into the cavity 14, for instance enzymes. The introduction of enzymes can convert damaged bases into single strand breaks, thus making it possible to directly assess the extent to which conditions lead to formation of certain classes of base lesions. In fact, the base lesions can even be quantified using systems, devices, and methods described herein, which in turn assist in knowing the cost-benefit of keeping or removing a particular DNA lesion for a particular person. In one embodiment, the cassette 10 can be modified to allow "flow-over" of solutions that contain various concentrations of DNA damaging agents. Such an embodiments makes it possible to perform DNA damage and repair assays on embedded cells. As an alternative, or in addition, to allowing "flow-over" of solutions, DNA damaging agents or other chemicals can be printed on the surface or allowed to diffuse into the matrix material 30 for specified time increments. For example, one or more chemicals can be printed on a membrane and the membrane can come into contact with a surface of the matrix material 30, thereby allowing one or more of the chemicals to diffuse into the matrix material 30. Alternatively, chemicals can be mixed into a gel to create a printed array of gel droplets, each containing a different component, as further provided below. These components can be chemicals at various concentrations, different types of chemicals, and/or different types of biologically active materials.

While the fluid can be used to lyse and unwind the nucleic acid, it can also be used to supplement and/or ultimately replace the material(s) that form the matrix material 30. More specifically, by flowing different fluids over a top surface of the matrix material 30, existing material of the matrix material 30 can be replaced by material from the fluid. This in turn allows for the cells 100 to be disposed in one or more types of materials, buffers, and reagents, and further, in materials, buffers, and reagents in which the cells 100 were not originally disposed. For example, a fluid can contain enzymes that modify the DNA, such as by endonucleolytic cleavage at sites of specific DNA lesions. Using the fluid to alter the properties of the matrix materials 30 allows for a wide range of tests to be performed that can not easily be performed using standard assays.

The flow of fluid from the inlet port to the outlet port can be achieved by manually introducing the fluid into the inlet port, or alternatively, by robotically controlling the flow of fluid between the inlet and outlet ports. It is generally preferred to automate the process robotically both to improve the standardization of such analyses and in particular to generate uniformity in reagent exchange. Similar to subtle changes in temperature and incubation times, even subtle changes in salt concentrations within a reagent has been shown to cause significant effects to the results of assays. (See Olive et al. 1992, Fairbairn et al. 1995, Klaude et al. 1996, and Hartmann et al. 2003.) In another embodiment, fluid can be placed onto a surface of the matrix material 30 using a robotic spotter.

Further, either before of after the matrix material 30 having cells 100 distributed to cell assay locations of the matrix material 30 interacts with the fluid delivery system, an additional layer of material can be introduced over the top of the matrix material. In some embodiments, this is a second matrix material, as discussed above with respect to FIGS. 8E and 9E and the second matrix materials 470, 870, respectively. The material can prevent cells from escaping from the matrix material 30, which can occur, for instance, when sheer forces from a fluid pass over a surface of the matrix material 30 and subsequently dislodge cells from recesses of the matrix material 30. The additional layer of material can be made of any of a number of materials, including agarose gel, a mesh including agarose, or any other material that is permeable such that fluids above the surface can penetrate to reach the cells embedded in the matrix material 30. When such material is added after the fluid is delivered to the cassette 10, this can allow for a final analysis to be generally performed using epifluorescent microscopy. Accordingly, it is preferred that the material of the additional layer does not interfere with image analysis. However, while the current analysis of DNA migration is performed using fluorescence, alternative methods can be applied to detect DNA migration, for example antibodies can be bound to the DNA and the antibodies can carry cargo that can be detected with means other than imaging, such as radioactivity.

Generally, if a cassette like the cassette 10 in FIG. 2B is used such that the matrix material is sandwiched by the top and bottom layers, once the matrix material is solidified, the gasket 20 can be removed and replaced with the gasket 22, which has a larger thickness and thus allows fluid to be introduced into the cavity 14. Alternatively, the gasket 20 can be configured such that its height can be expanded. In another embodiment, sufficient space can be left in the initial construction of the cassette 10 such that no such substitution or expansion is needed to allow fluid to be introduced into the cavity 14. As illustrated in FIG. 2C, running the fluid across the matrix material 30 causes convection and diffuses the matrix material in a generally downward direction. Once the fluid has been run through the cavity 14, the electrophoreses matrix material 30 is ready to be analyzed, a process which will be discussed in further detail below.

As an alternative to a fluid delivery system, one or more applicators can be used to introduce one or more reagents to the matrix material. The matrix material can be disposed in a cassette or a receptacle as described above, and the applicator can be any number of devices configured to apply a fluid to a desired location. In one exemplary embodiment the applicator is a pipette. In embodiments that use two or more applicators to introduce two or more reagents, the applicators can be the same applicator or they can be different applicators, although it is generally preferred to use a second and separate applicator such that any residue from the first applicator and/or the first reagent does not mix with the second reagent. The reagents used can be the same reagent or different reagents, depending on the desired testing protocol and analyses that are being performed. Like many of the disclosures herein, variations related to the types of materials used, the designs of the devices and methods, etc. will depend on what the user is attempting to analyze, and the methods, devices, and systems taught herein provide a great deal of versatility in that respect.

Once the fluids are run through the cassette 10, the matrix material 30 can be removed from the cassette 10 and immersed in an electrophoresis chamber. The matrix material 30 can be removed using any number of methods, for instance by removing any layers above the matrix material 30 (e.g., the top slide 16 and the gasket 22 in FIG. 2C). When the matrix material 30 is coupled to a bottom layer, such as the bottom slide 18, if the layer is transparent it does not need to be removed, although it can be if configured to do so. Alternatively, electrodes can be incorporated into the cassette 10, as discussed above and further below, which in turn allows electrophoresis to be performed within the cassette 10 without removing the matrix material 30.

One of the benefits of a self-contained electrophoresis assay cassette is that it allows for various conditions to be kept uniform across tests, whether performed by the same or different individuals or the same or different laboratories. For example, the cassette 10 can control the thickness of the matrix material 30 such that the cells 100 can be aligned by sedimentation prior to solidifying the matrix material 30, and additionally, the fluid flow can be integrated and controlled robotically so that uniformity is created in the reagent exchange. The cassette 10 also allows the samples to be protected from inadvertent DNA damage that can be occur, for instance, exposure to ultraviolet light that can occur during sample handling. In addition to some of the standardization techniques already discussed herein, the cassette 10 can further include additional features to make a more uniform environment. For example, temperature control microdevices can be included in the cassette 10 to regulate the temperature inside the cassette 10 throughout the duration of its use. Such devices can reduce the time for incubation steps because membrane lysis and DNA denaturation can be accelerated by higher temperatures, which can be created by such temperature control microdevices. By way of further example, oxygen tension can be controlled, which is particularly advantageous because in current comet assays exposure to oxygen tension of ambient air can introduce undesirable DNA damage.

Further, electrical fields or electrodes can be engineered into the cassette 10 so that electrophoresis can be performed on-chip, thus allowing the electrophoresis process to be substantially standard between all cassettes. Not only does this allow for improved standardization, but it can also allow for a faster, more sensitive assay. Currently, traditional comet assays run at a specified voltage. In light of the present disclosures, the voltage and/or amperage can be modulated to potentially speed up the assay and/or increase the sensitivity of the assay. Pulsed field electrophoresis conditions can be applied to increase the tail lengths and thus increase the sensitivity of the assay. Still further, because of the constituency and reliability of the cassette 10, it also creates much more uniform incubation times for running the assays. It is widely recognized that inconsistent incubation times can drastically affect the results of the assays. Nevertheless, a person skilled in the art will recognize that while the cassette 10 greatly improves the uniform nature of running an electrophoresis assay, completely removing variations that exist between tests is virtually impossible.

A further benefit of the cassette 10 is that it can be produced relatively cheaply and efficiently, which in turn makes it useful as a disposable cassette. A disposable cassette further enhances standardization because each cassette is new and no materials from a previous assay can be located in the cassette to cause unwanted noise.

In one exemplary embodiment of a self-contained electrophoresis assay cassette, the cassette is substantially automated. A matrix material having cell assay locations with cells disposed at least partially therein can be automatically created by mixing and solidifying the matrix material in an automated fashion either outside or inside the cassette. Placement of the matrix material having cells disposed at least partially therein can be performed by a machine or robot, and then arraying, processing, staining, and analyzing the cells of the matrix material can all be performed using automated devices. Such automation reduces the amount of labor needed to run assays, increases consistency of the assays, and increases throughput.

In one embodiment, a self-contained electrophoresis assay cassette can be connected to a shunt system. The shunt system can be configured to remove one or more cells from a location, circulate the cells to the cassette for analysis thereof, and then remove the cells from the cassette, back through the shunt, to return them to a desired location. Such a system preferably includes a cassette that is configured for automated analysis. The system is useful in a variety of capacities, but particularly for analyzing tumor cells.

There are additional benefits of using a self-contained electrophoresis assay cassette worth noting. For example, the matrix material 30 does not need to be removed from the cavity 14 after it has been run and stained. Because the matrix material 30 is generally fragile and complications can arise in handling the matrix material 30, reducing the amount of handling of the matrix material 30 is desirable because results in less damaged and unusable matrix material 30. Accordingly, fewer matrix materials are damaged and materials to form the same are conserved. This is in addition to the fact that less material can be used to form each matrix material in light of the disclosures herein. Further, because the cassette 10 can create a substantially uniform, thin matrix material 30, which is generally conducive to enhanced electrophoresis performance, the separation of very high molecular weight DNA can be improved because the resulting signal-to-noise ratio is improved. A thinner matrix material also significantly reduces incubation times. While in previous comet assays the density of the matrix material had to be sufficiently high to assure that it stayed intact during manipulation, an enclosed chamber allows for a lower density matrix material because such manipulations are less frequent and less traumatic. Still further, because the cassette 10 has the capacity to run buffers over the surface of the matrix material 30, gradient conditions can be applied that may improve assay sensitivity.

Just as a self-contained electrophoresis assay cassette provides many benefits, especially with respect to standardization of assay measurements, matrix materials having desired arrays also greatly improve assay measurements. Aside from some of the benefits already discussed with respect to speed and efficiency based on the number of samples that can be analyzed at a time and standardization based on being able to locate samples at uniform locations during various tests, one of the greatest benefits afforded by matrix materials having desired arrays is the flexibility of tests that can be performed. Some examples of these testing procedures that can be used in light of the teachings herein include: testing the response of the same cell type from the same person to the same reagent (to determine any anomalies for instance); testing the response of the same cell type from multiple people to the same reagent; testing the response of multiple cell types from the same person to the same reagent; testing the response of the same cell type from the same person to multiple reagents; testing the response of the same cell type from multiple people to multiple reagents; and testing the response of multiple cell types from multiple people to multiple reagents. The testing of multiple cells and/or multiple conditions on the same matrix material is highly desirable from both an efficiency and a consistency standpoint. Further, locating cells in an array allow a higher percentage of cells to be analyzed because there is not a problem of tails from one cell overlapping with another cell. Still further, because multiple samples can be run at the same time, the disclosures herein allow the effects of time to be more easily analyzed. More particularly, by running multiple samples at the same time and comparing similar samples run at a different time, the effect of time on the cells can be compared more accurately because now multiple results can be generated for one time period.

As discussed above, in some embodiments matrix materials can be layered at least partially on top of each other. Not only does such a set-up allow for increased speed and efficiency, but it also allows for additional types of tests to be performed, for instance tests related to the study of cell-to-cell interactions. One example of a cell-to-cell interaction test includes disposing a first matrix material having a sample of cells distributed to cell assay locations of the matrix material located on top of a second matrix material having a sample of cells distributed to cell assay locations of the second matrix material to investigate the impact of cell proximity on DNA damage and repair in adjacent or nearby cells. In one exemplary embodiment for studies of primary cells, such as hepatocytes, stromal cells can be integrated so that DNA repair can be assessed in primary hepatocytes that behave in a manner that is more consistent with the in vivo conditions. Any number of layers of matrix materials can be used, and layers can be added and subtracted from any location as desired. Further, in lieu of, or in addition to using individual layers, a single matrix material can have multiple layers of cells disposed therein.

Figure 11A:
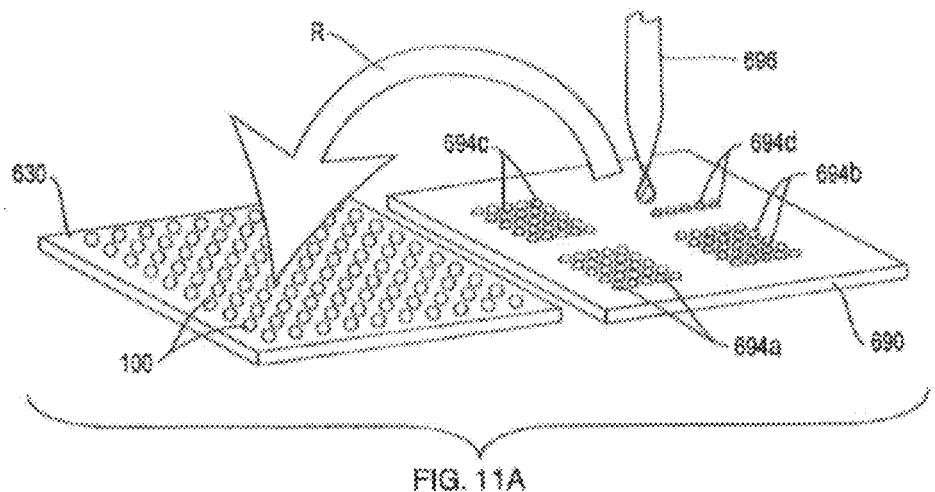
FIG. 11A is a perspective view of one exemplary embodiment of a system for nucleic acid analysis employing a reagent applying overlay.

One exemplary method of multiplexing for performing the types of tests discussed above is illustrated in FIG. 11A. A multi-site matrix material 630 having a plurality of cells 100 captured on it is provided. An overlay 690 that is configured to have one or more testing reagents, drugs, and/or hydrogels disposed thereon is also provided. In the illustrated embodiment the overlay 690 includes four different hydrogels 694a, 694b, 694c, and 694d, each containing a different testing reagent, and each of which is optionally located on a separate region of the overlay 690. By providing multiple types of testing reagents, the multiplexing becomes addressable, that is, different reagents can be targeted to different cell types. The hydrogels 694a, 694b, 694c, and 694d can be applied to the overlay 690 in a number of different manners, but in the illustrated embodiment a pipette 696 is used to apply the hydrogels 694a, 694b, 694c, and 694d in a bead configuration. In alternative embodiments the testing reagents can be disposed in one or more larger hydrogels that can then be applied to the matrix material 630 at least in a similar fashion as the illustrated embodiment. Once the desired number of testing reagents is disposed on the overlay 690, the overlay 690 can be applied to at least a portion of the matrix material 630, for instance by flipping the overlay 690 onto the matrix material 630 as illustrated by arrow R. Flipping the overlay 690 onto the matrix material 630 can allow the reagents to diffuse from the hydrogels 694a, 694b, 694c, and 694d and into the cells 100 on the multi-site matrix material 630. Tests can then be performed to determine the effect of the reagents on the cells 100.

Figure 11B:
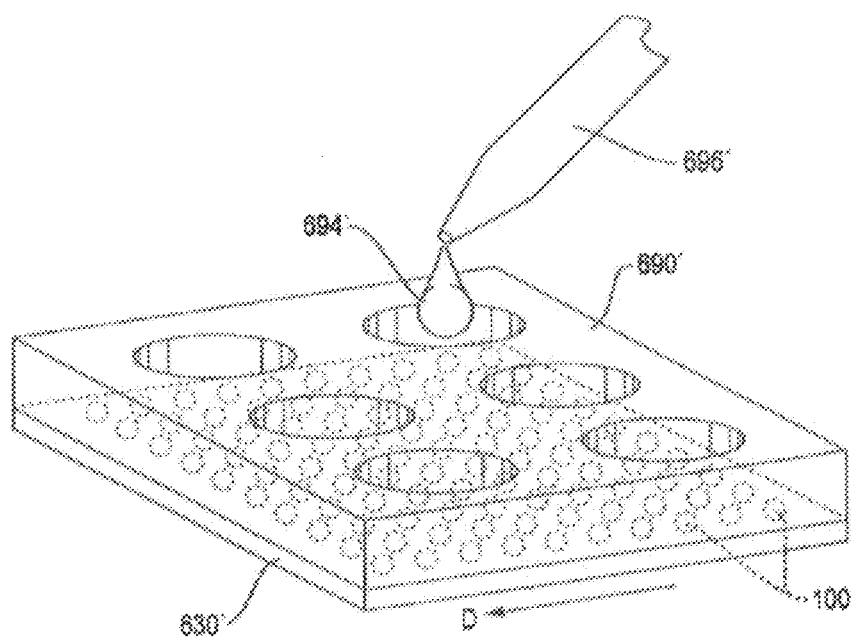
FIG. 11B is a partially transparent perspective view of another exemplary embodiment of a system for nucleic acid analysis employing a reagent applying overlay.

Another method of multiplexing for performing the types of tests discussed above is illustrated in FIG. 11B. A multi-site matrix material 630' having a plurality of cells 100 captured on it is provided. An overlay 690' configured to allow one or more testing reagents 694' to be applied to one or more of the cells 100 on the matrix material 630' can be located above the matrix material 630'. In the illustrated embodiment the overlay 690' includes a plurality of macrowells 692' that allow the reagent 694' to pass through the overlay 690' and onto cells 100 of the matrix material 630'. Although macrowells 692' are used in the illustrated embodiment, any number of designs to achieve the same purpose can be used, including microwells that substantially align with desired capture sites located on the matrix material 630'. The reagent 694' can be applied to the overlay 692' by any number of applicators, including for example a pipette 696'. The overlay 692' can be moved in any desired direction, for example direction D as illustrated, to apply the reagent 694' to the cells 100 on the matrix material 630'. Movement of the overlay 692' allows the reagents 694 to be selectively applied to various portions of the matrix material 630' and to various cells 100 in particular. In one embodiment drug-bearing hydrogels can be located near the overlay, or even in the macrowells 692', to allow reagents from the drug-bearing hydrogels to be easily applied to the overlay 690', and subsequently the cells 100 on the matrix material 630'.

These two general multiplexing methods allow for multiple reagents to be tested on a multi-site matrix material in a plug-and-play fashion. In still another embodiment no overlay is used and the reagents are robotically spotted directly onto a multi-site matrix material like the matrix materials 630, 630'. A robotic-spotting system, such as the PixSys non-contact liquid handling system from Digital Genomic Solutions, includes unique features that are useful for a fully-multiplexed DNA damage and repair assay. Such a system allows the creation of arrays of DNA damaging agents, covering a wide range of solutions from aqueous to solvent-based small molecules. In one embodiment the system has two independently controlled liquid channels, which allows for the creation of custom combinations of reagents to be used to understand the complex synergistic effects of combined exposures. (Lee et al. 2005 and/or 2008) Such a system can spot 50 or more matrix materials in one run, which enables relatively large-scale studies. Additionally, because these systems utilize non-contact spotting, the overlays 690, 690' can be eliminated such that the reagents can contact the matrix material 630, 630' without damaging it.

Figure 12:
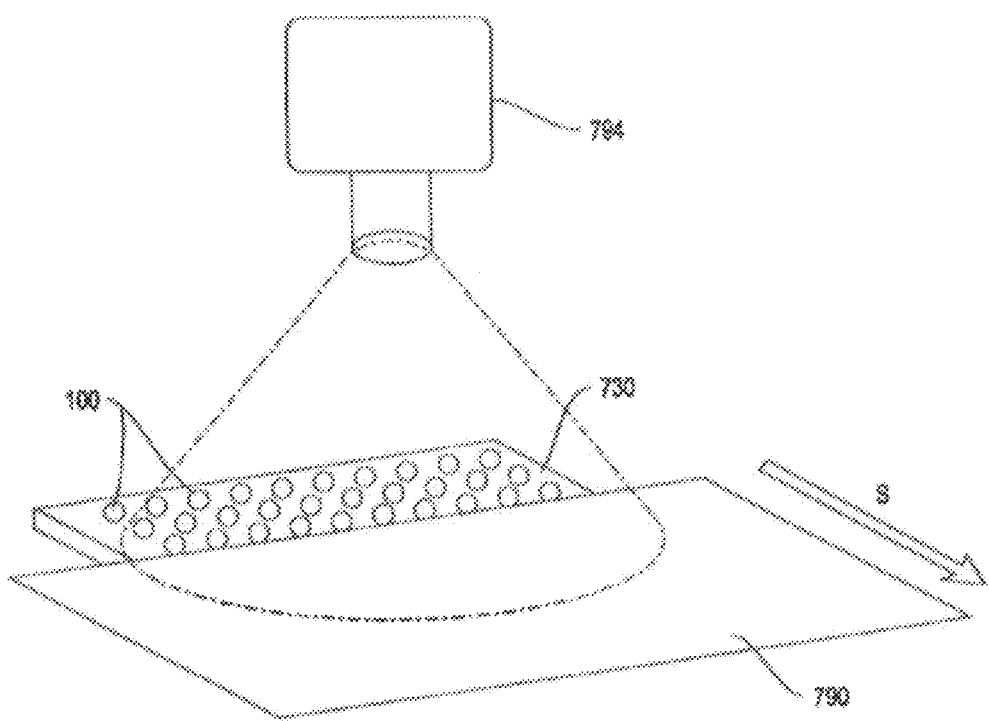
FIG. 12 is a perspective view of one exemplary embodiment of a system for determining multiple exposure conditions.

FIG. 12 illustrates a further exemplary method for testing various responses of cells to various exposure conditions by multiplexing. A multi-site matrix material 730 having a plurality of cells 100 captured on it is provided. Located above the matrix material 730 is a template that is configured to selectively regulate exposures of the cells 100 to one or more conditions. In the illustrated embodiment the template is a shield 790 configured to block exposure conditions generated by an electromagnetic radiation source 794. The shield 790 can be moved in a desired direction S to selectively control the amount of exposure particular cells 100 on the matrix material 730 experience. Various cells 100 can thus be exposed to various exposure doses, and then once exposure is complete, the matrix material 730 can be placed in a lysis solution so a comet assay can be conducted. Movement of the shield 790 can be done manually or it can be automated, and like any of the testing procedures discussed herein, such movement is performed based on the desire of the user. In one embodiment the template is made of lead and the electromagnetic radiation source provides x-rays. Alternatively, the template can have one or more designs incorporated into it such that some cells are exposed to the radiation source while others are not when the template is located in a particular position. A user can adjust the particular position of the template based on the intended use of the system. While this system and method is described with particular reference to conditions created by electromagnetic radiation, other conditions could also be used with this system, such as reagent delivery.

One useful application of the systems, devices, and methods disclosed herein is for use as a biomarker of inflammation. This is at least because reactive oxygen and nitrogen species are known to induce DNA damage, and thus the systems, devices, and methods can be configured to assist with inflammation issues. Another useful application of the systems, devices, and methods disclosed herein is applying them to determine how a minority population of cells responds to DNA damage. More specifically, the systems, devices, and methods disclosed allow for a single cell to be tested amongst a great many number of cells, meaning its reaction alone can be tested without being masked by a majority of cells that only get tested because of the time it takes to run a single assay using current systems, devices, and methods.

Still a further useful application of the systems, devices, and methods disclosed herein is using them to evaluate the effect of cell cycle phase on the results of some of the methods. Cell cycle phase can be evaluated by assessing the total amount of DNA per cell or by cell cycle specific staining techniques, such as Bromodeoxyuridine. This information can be overlaid so that the extent of DNA damage is evaluated at specific cell cycle stages. On a related note, the slide can potentially be registered so that image analysis can be done at various times during an analysis. For example, a mixture of cell types can be placed into wells, can be stained for particular markers, and can subsequently be analyzed for DNA damage levels. By aligning the registration, specific wells can be analyzed for different characteristics at different times. As a result, it is possible to assess DNA damage levels among cells within a mixed population of cell types. In one application, many cell samples can each be labeled with a different tag, such as q-dots or Celltracker dyes. Each cell within the array can be evaluated for specific markers, subsequently cells can be lysed, and electrophoresis can be run. Spatial encoding allows correlation between specifically tagged cells and their DNA damage levels. With respect to overlaying cell type information with DNA damage and repair information, one example of use can be found in a population of cancer cells where cancer stem cells can be labeled and analyzed for their levels of DNA damage and/or repair capacity. Some examples of cancer cells that can be analyzed include ovarian carcinoma cells lines such as OV5, OV8, and SKOV-3x. In one exemplary embodiment, ovarian carcinoma cell lines can be located at cell capture sites on a matrix material and their response to a particular chemical, such as AP endonuclease 1, can be tested. AP endonuclease 1 has been shown to have the potential as an anti-cancer target, and tests to determine its usefulness with respect to various cancer types can be useful. Other chemicals and treatments can likewise be tested quickly and efficiently using the systems, devices, and methods discussed herein.

Yet another useful application of the systems, devices, and methods disclosed herein is using them in conjunction with drug discovery. For example, DNA repair inhibitors can be analyzed. Different cells can be disposed on a matrix material and various DNA repair inhibitors can be tested on various cells to test their effectiveness. This can be particularly useful in cancer chemotherapy, where DNA repair inhibitors have been shown to be effective in treatment.

Figure 13:
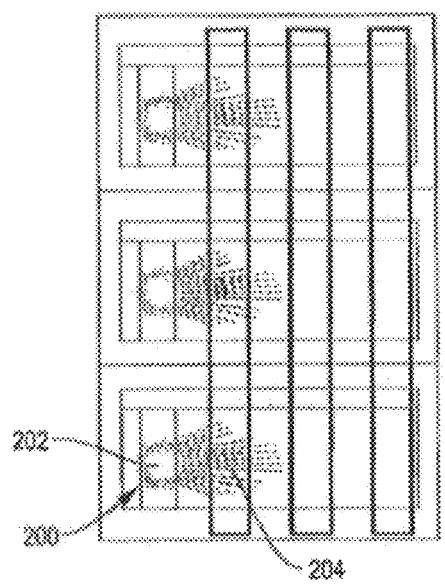
FIG. 13 is a partial schematic top view of an image resulting from performing electrophoresis on the matrix material of FIG. 3.

Whether using a self-contained electrophoresis assay cassette, a matrix material, or any other device, system, or method discussed herein, once the cells disposed on a matrix material have been exposed to one reagent, electrophoresis can be performed on the cells. Generally this involves applying an electric field to the assay such that the portions of the nucleic acids that are damaged or repaired migrate away from the central portion of the cells. Typically the nucleic acid is negatively charged and the electric field is positively charged. The central portion of the cells, which generally consists of undamaged DNA, is supercoiled and highly compact, while the damaged and/or repaired portions generally become relaxed loops or fragments after the reagent is applied to the cell. As a result, the relaxed loops or fragments generally more readily migrate than the supercoiled portions within the nucleoid, which in turn results in the comet-shaped image. The two characteristics that generally dictate the level of travel for the damaged and/or repaired portions are the size and superhelicity of the fragments. Applying fluorescence to the resulting matrix material can then reveal images such as the ones shown in FIG. 13. More particularly, FIG. 13 illustrates a partial result from an electrophoresis analysis performed on a matrix material having a grid array like the grid 132 of the matrix material 130 of FIG. 3. Each cell generally looks like a comet 200 having a bright nucleoid 202 representing the undamaged portion and a comet-like tail 204 representing the damaged and/or repaired portions of the nucleic acid. Depending on the conditions and desired testing procedures, the assay can be optimized to detect double strand break, single strand breaks/alkali sensitive sites, and certain classes of DNA base lesions.

A variety of methods can be used to collect and analyze the data resulting from the electrophoresis being performed on the cells of the matrix material. In some instances, a user can visually classify the results, although in a preferred embodiment the matrix material is analyzed using image analysis software to classify the results, for instance be assessing the extent to which DNA has been pulled away from each nucleoid. More specifically, the data from the matrix material can be scanned using a 20× objective, isolating single cells, and bringing them into focus. The user can then select the area of the image desired for further analysis using a software program, such as Komet 5.5. To use the Komet 5.5 program, a "region of interest" window is overlayed onto the fluorescent nucleus and the software program automatically assess the area, identifies the region of high density, i.e. the nucleoid, and attains a density plot in which the brightest region is considered to be the center. The program then applies a symmetry parameter that defines the edges of the nucleus using the assumption that the nucleus is symmetrical, in which case the comets need to be pre-oriented in the appropriate direction. The program then defines a preset region of predetermined size above the nucleus and it considers this region as being "background" signal. After excluding the nucleus, the program then queries the area where the tail is expected to be located to ascertain pixels that are significantly above background levels of fluorescence. It then analyzes the comet for a variety of parameters, including optical density, tail length, percentage of total optical density present in the tail, etc. Generally the Olive Tail Moment, which is discussed in more detail below, is plotted in most experiments.

While the Komet 5.5 program typically uses a symmetry parameter, such a restriction is not necessary in light of the disclosures herein. Analysis of the migration of nucleic acids can be analyzed independently of symmetry of the nucleoid. For single cells, the shape of the nucleus can be affected by the size and/or shape of the microwell, thus distorting the nucleoid and rendering traditional image analysis programs obsolete. For microwells, image analysis can be performed under conditions that do not apply a symmetry parameter and instead take into consideration the addresses and edges of the microwells (or other type of cell assay location). Further, spatial patterning provides the ability to perform bulk-image analysis such that the extent to which nucleic acids have migrated away from multiple microwells can be assessed as a single parameter. Image analysis can be significantly expedited by bulk processing of comet tails from multiple cells. Additionally, bulk processing reduces the volume of data that is processed per sample.

An optical imaging station is an alternative mechanism that can be used to collect and analyze data. An optical imaging station is capable of automatically collecting data, thereby avoiding tedious steps such as isolating single cells and bringing them into focus. For example, Metasystems has combined a microscope, a robotic platform that can be programmed to move in the x, y, and z directions, and specialized computer software together into a single image analysis platform. This imaging platform is capable of automatically analyzing thousands of comets in light of the disclosures herein. This equipment scans a specified area, identifies fluorescent nucleoids, creates addresses for each nucleoid, and then returns to each nucleoid and automatically focuses and collects an image. It then automatically overlays the appropriate analysis framework and compiles the data into a spreadsheet. What can take an average person about 30 minutes to accomplish can be reduced to under 3 minutes. Simply by combining many comet assays as produced by the disclosures herein and applying this type of analysis platform, it can be feasible to analyze every well of a 96 well plate automatically, and can be accomplished in the same amount of time that analysis of a single sample can require.

Similar to the Komet 5.5 program, traditional image analysis is also improved upon as a result of the disclosures herein. Physical placement of cells in a microwell permits new methods for analyzing nucleic acid migration. For example, rather than using the nucleoid as the reference point for the distance of tail migration, the microwell itself can be used as a reference point. Further, to facilitate analysis, fluorescent particles that do not migrate a significant amount during electrophoresis can be added to the microwell such that the perimeter of the well can be evaluated as a parameter when considering the amount of nucleic acid and the distance traveled by the nucleic acid away from the microwell.

Figure 14A:
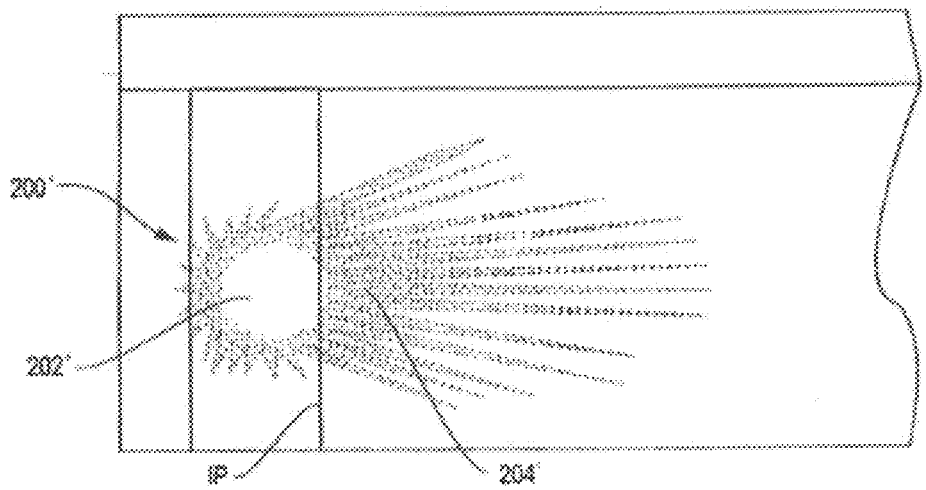
FIG. 14A is a schematic top view of an image resulting from performing electrophoresis on a single cell assay location on a matrix material.
Figure 14B:
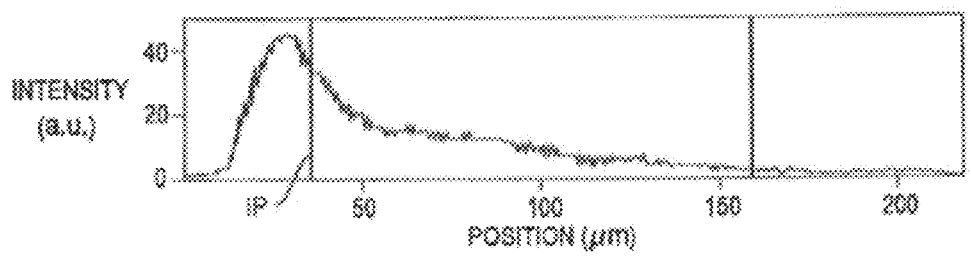
FIG. 14B is a chart resulting from image analysis performed at the single cell assay location of FIG. 14A.

In one embodiment automated image analysis of arrayed cells can be achieved with the use of a program configured to provide image analysis and a microscope in conjunction with the methods and devices disclosed herein. While Komet 5.5 is discussed above as one example of such a program, in another program the present invention allows for more accurate readings of arrayed cells, and even allows for accurate readings in instances when multiple cells are located in a single well of a matrix material. This is at least because microwells formed in a matrix material can provide a useful marking location for image analysis. As illustrated in FIG. 14A, a comet 200' having a bright nucleoid 202' representing the undamaged portion and a comet-like tail 204' representing the damaged and/or repaired portions of the nucleic acid can result from applying fluorescence to a resulting matrix material as discussed with respect to FIG. 13 above. A line IP illustrates the division between the nucleoid 202' and the tail 204'. As illustrated in FIG. 14B, an inflection point in the intensity of the comet 200' occurs at the exact same location where the nucleoid 202' is separate from the tail 204', as shown by line IP. Precisely locating the line IP to separate the nucleoid 202' from the tail 204' necessarily leads to more accurate measurements. More specifically, because of the wells of the matrix material, an inflection point is formed at the precise location where the nucleoid 202' and the tail 204' of the comet 200' split.

An unexpected interface occurs between the inside of the well and the edge of the well that causes the inflection in DNA intensity. This inflection point offers a powerful advantage for automated image analysis because it provides accuracy never experienced before. Use of this noticeable inflection point can prevent incorrect analysis of comets and thus can reduce or eliminate the time-consuming step of identifying by eye misanalyzed comets that should be removed from a data set. A person skilled in the art will recognize the importance of removing misanalyzed comets from a data set in order to have accurate results. Additionally, use of the inflection point provides the ability to analyze wells having multiple cells disposed therein. Combining these findings with a microscope, such as a Nikon automated fluorescent microscope, can allow for fully automated imaging and analysis.

In one exemplary embodiment a first program scans 10× resolution images for objects defined by a threshold intensity. Objects that fall outside the defined microwell matrix or that are too close to the edge are eliminated as debris while the arrayed comets are cropped for individual analysis. A second program can then use a line intensity plot, as illustrated in FIG. 14B, to score the resulting comets for a variety of parameters, for example percent DNA in the nucleoid or head, the percent DNA in the tail, the Olive tail moment, and the tail length. The nucleoid diameter can be determined as the local minimum of the first derivative of the intensity plot, taking advantage of the fixed well size to provide a predictive search window. Comets that are unable to be analyzed can be screened using pre-determined thresholds, which can be created, for example, by relying on training sets produced by a manual version of image analysis.

Automated programs used in conjunction with a microscope can dramatically decrease process and analysis times, take advantage of spatial encoding to screen out debris, and calculate nucleoid diameters through calculus-based edge finding. Instead of one image per comet, a lower magnification image can be used and nine or more comets per image can be analyzed. This not only increases efficiency, but it also reduce memory demand. Further, the use of the automated programs can eliminate inherent bias and errors that can occur using manual comet selection analysis programs by automatically selecting comets from the defined array. The selection of comets can be helped by the fact that the configurations of the matrix materials and arrays discussed herein can be defined by labeling and spatial encoding. Still further, the automated programs can be tied into a user interface that also has automated data analysis capabilities to provide further ways to use the data provided by the systems, devices, and methods discussed herein.

Other methods of DNA imaging can also be used in conjunction with the present disclosures. For example, DNA can be stained with ethidium bromide, or alternatively it can be stained with SYBR green, Fluorescein Isothiocyanate conjugated antibodies, or other useful molecules. Furthermore, the use of various fluorescently tagged antibodies can permit the analysis of certain DNA structures, such as single stranded DNA, which is increasingly recognized as an important indicator of genomic damage.

Preferably any analysis of the matrix material is directed to at least one of the following three parameters: the Percent Tail DNA, which is simply a measure of how much of the DNA is in the tail compared to the "head" or nucleoid of the assay; the tail length, which is generally measured in microns, and the Olive Tail Moment, which is a calculation that combines the two aforementioned parameters–OliveTailMoment=(TailMean–HeadMean)×PercentTailDNA/100 (Burlinson et al. 2006.) Even with the more standardized, uniform testing resulting from the systems, devices, and methods discussed herein, it is important to realize that each cell is unique and thus even from cell to cell in a standardized system there can be variations in the value of the tail moment. This is the case for a comet assay, regardless of the method, the conditions, or the cell type. The disclosed systems, devices, and methods, however, significantly reduce these variations both by creating a more uniform local environment to provide more accurate results and by allowing more tests to be run in a short period of time, thereby providing more data be analyzed and further improving accuracy.

Further, materials related to the methods, systems, and devices disclosed herein include the following, each of which are hereby incorporated by reference in their entireties:

Ager D D, Dewey W C, Gardiner K, Harvey W, Johnson R T et al. (1990) Measurement of radiation-induced DNA double-strand breaks by pulsed-field gel electrophoresis. Radiat Res 122(2): 181-187.

Aka, Peter Micheline Kirsch-Volders, et al. (2004) "Are genetic polymorphisms in OGG1, XRCC1 and XRCC3 genes predictive for the DNA strand break repair phenotype and genotoxicity in workers exposed to low dose ionising radiations?" *Mutation Research/Fundamental and Molecular Mechanisms of Mutagenesis.* Volume 556|1-2:22.

Al-Fageeh M B, Smales C M (2006) Control and regulation of the cellular responses to cold shock: the responses in yeast and mammalian systems. Biochem J 397(2): 247-259.

Al-Tassan N, Chmiel N H, Maynard J, Fleming N, Livingston A L et al. (2002) Inherited variants of MYH associated with somatic G:C-->T:A mutations in colorectal tumors. Nat Genet 30(2): 227-232.

Alapetite C, Wachter T, Sage E, Moustacchi E (1996) Use of the alkaline comet assay to detect DNA repair deficiencies in human fibroblasts exposed to UVC, UVB, UVA and gamma-rays. Int J Radiat Biol 69(3): 359-369.

Albrecht D R, Sah R L, Bhatia S N (2004) Geometric and material determinants of patterning efficiency by dielectrophoresis. Biophys J 87(4): 2131-2147.

Albrecht D R, Tsang V L, Sah R L, Bhatia S N (2005) Photo- and electropatterning of hydrogel-encapsulated living cell arrays. Lab Chip 5(1): 111-118.

Albrecht D R, Underhill G H, Wassermann T B, Sah R L, Bhatia S N (2006) Probing the role of multicellular organization in three-dimensional microenvironments. Nat Methods 3(5): 369-375.

Allen J W, Khetani S R, Bhatia S N (2005) In vitro zonation and toxicity in a hepatocyte bioreactor. Toxicol Sci 84(1): 110-119.

Allen J W, Khetani S R, Johnson R S, Bhatia S N (2006) In Vitro Liver Tissue Model Established from Transgenic Mice: Role of HIF1alpha on Hypoxic Gene Expression. Tissue Eng.

Andreoli C, Leopardi P, Crebelli R (1997) Detection of DNA damage in human lymphocytes by alkaline single cell gel electrophoresis after exposure to benzene or benzene metabolites. Mutat Res 377(1): 95-104.

Azqueta A, Shaposhnikov S, Collins A R. (2009) "DNA oxidation: Investigating its key role in environmental mutagenesis with the comet assay." *Mutat Res.* 674|1-2: 101-8.

Bacso Z, Everson R B, Eliason J F (2000) The DNA of annexin V-binding apoptotic cells is highly fragmented. Cancer Res 60(16): 4623-4628.

Bapat, Aditi Melissa L. Fishel, Mark R. Kelley. (2009) "Going Ape as an Approach to Cancer Therapeutics." *Antioxidants & Redox Signaling*. Vol. 11, No. 3: 651-668.

Barlow C, Hirotsune S, Paylor R, Liyanage M, Eckhaus M et al. (1996) Atm-deficient mice: a paradigm of ataxia telangiectasia. Cell 86(1): 159-171.

Bauch T, Bocker W, Mallek U, Muller W U, Streffer C (1999) Optimization and standardization of the "comet assay" for analyzing the repair of DNA damage in cells. Strahlenther Onkol 175(7): 333-340.

Beard W A, Osheroff W P, Prasad R, Sawaya M R, Jaju M et al. (1996) Enzyme-DNA interactions required for efficient nucleotide incorporation and discrimination in human DNA polymerase b. J Biol Chem 271(21): 12141-12144.

Berdal K G, Johansen R F, Seeberg E (1998) Release of normal bases from intact DNA by a native DNA repair enzyme. EMBO J 17(2): 363-367.

Berwick, Marianne Paolo Vineis. (2000) "Markers of DNA Repair and Susceptibility to Cancer in Humans: an Epidemiologic Review." *Journal of the National Cancer Institute*. Volume 92|11:874-897.

Bhalli J A, Khan Q M, Nasim A (2006) DNA damage in Pakistani pesticide-manufacturing workers assayed using the Comet assay. Environ Mol Mutagen 47(8): 587-593.

Bhatia et al. (1994) "Selective Adhesion of Hepatocytes on Patterned Surfaces" *Annals of the New York Academy of Sciences*. Volume 745|8:187-209.

Bhatia S N, Yarmush M L, Toner M (1997) Controlling cell interactions by micropatterning in co-cultures: hepatocytes and 3T3 fibroblasts. J Biomed Mater Res 34(2): 189-199.

Bhatia S N, Balis U J, Yarmush M L, Toner M (1999) Effect of cell-cell interactions in preservation of cellular phenotype: cocultivation of hepatocytes and nonparenchymal cells. Faseb J 13(14): 1883-1900.

Botta C, Iarmarcovai G, Chaspoul F, Sari-Minodier I, Pompili J et al. (2006) Assessment of occupational exposure to welding fumes by inductively coupled plasma-mass spectroscopy and by the alkaline Comet assay. Environ Mol Mutagen 47(4): 284-295.

Branch D W, Corey J M, Weyhenmeyer J A, Brewer G J, Wheeler B C (1998) Microstamp patterns of biomolecules for high-resolution neuronal networks. Med Biol Eng Comput 36(1): 135-141.

Bryant, Helen, Thomas Helleday, et al. (2005) "Specific killing of BRCA2-deficient tumours with inhibitors of poly (ADP-ribose) polymerase." *Nature*. Volume 434.

Burger S, Schindler D, Fehn M, Muhl B, Mahrhofer H et al. (2006) Radiation-induced DNA damage and repair in peripheral blood mononuclear cells from Nijmegen breakage syndrome patients and carriers assessed by the Comet assay. Environ Mol Mutagen 47(4): 260-270.

Burlinson, Brian (Glaxo Wellcome). (2003) "Comet Assay: A crucial method for examining DNA damage and repair." United Kingdom Environmental Mutagen Socieity Conference.

Burlinson B, Tice R R, Speit G, Agurell E, Brendler-Schwaab S Y et al. (2006) Fourth International Workgroup on Genotoxicity testing: Results of the in vivo Comet assay workgroup. Mutat Res in press.

Calini, V, Urani C, Camatini M, (2002) "Comet assay evaluation of DNA single- and double-strand breaks induction and repair in C3H10T1/2 cells." *Cell Biol Toxicol.* 18|6: 369-79.

Carrera, Navarette, et al. (1998) "In vivo response of mouse liver to g-irradiation assessed by the comet assay." *Mutation Research*. Volume 413|1.

Cebulska-Wasilewska A, Wiechec A, Panek A, Binkova B, Sram R J et al. (2005) Influence of environmental exposure to PAHs on the susceptibility of lymphocytes to DNA-damage induction and on their repair capacity. Mutat Res 588(2): 73-81.

Chen B, Vu C C, Byrns M C, Dedon P C, Peterson L A (2006) Formation of 1,4-dioxo-2-butene-derived adducts of 2'-deoxyadenosine and 2'-deoxycytidine in oxidized DNA. Chem Res Toxicol 19(8): 982-985.

Chen C S, Mrksich M, Huang S, Whitesides G M, Ingber D E (1997) Geometric control of cell life and death. Science 276(5317): 1425-1428.

Chin V I, Taupin P, Sanga S, Scheel J, Gage F H et al. (2004) Microfabricated platform for studying stem cell fates. Biotechnol Bioeng 88(3): 399-415.

Clark P, Britland S, Connolly P (1993) Growth cone guidance and neuron morphology on micropatterned laminin surfaces. J Cell Sci 105 (Pt 1): 203-212.

Cleaver J E (1968) Defective repair replication of DNA in xeroderma pigmentosum. Nature 218: 652-656.

Collins, Angelis et al. (1999) "Single cell gel electrophoresis: Detection of DNA damage at different levels of sensitivity." *Electrophoresis*. Volume 20:2133-2138.

Collins. Andrew (2009) "Investigating oxidative DNA damage and its repair using the comet assay." *Mutation research*. Vol. 681|1: 24-32.

Collins A R (2004) The comet assay for DNA damage and repair: principles, applications, and limitations. Mol Biotechnol 26(3): 249-261.

Collins A R, Dusinska M, Horvathova E, Munro E, Savio M et al. (2001) Inter-individual differences in repair of DNA base oxidation, measured in vitro with the comet assay. Mutagenesis 16(4): 297-301.

Cox M M (2001) Recombinational DNA repair of damaged replication forks in *Escherichia coli*: questions. Annu Rev Genet. 35: 53-82.

Dabhokar, Reed, et al. (1993) "Expression of excision repair genes in nonmaligant bone marrow from cancer patients." *Mut Res.* 293|2:151-156.

Damia, Imperatori, Stefanini, D'Incalci. (1996) "Sensitivity of CHO mutant cell lines with specific defects in nucleotide excision repair to different anti-cancer agents." *Int. J. Cancer.* Volume 66:779-783.

Daya-Grosjean L, Sarasin A (2005) The role of UV induced lesions in skin carcinogenesis: an overview of oncogene and tumor suppressor gene modifications in xeroderma pigmentosum skin tumors. Mutat Res 571(1-2): 43-56.

Dedon P C, Tannenbaum S R (2004) Reactive nitrogen species in the chemical biology of inflammation. Arch Biochem Biophys 423(1): 12-22.

Dong M, Dedon P C (2006) Relatively small increases in the steady-state levels of nucleobase deamination products in DNA from human TK6 cells exposed to toxic levels of nitric oxide. Chem Res Toxicol 19(1): 50-57.

Doulias P T, Barbouti A, Galaris D, Ischiropoulos H (2001) SIN-1-induced DNA damage in isolated human peripheral blood lymphocytes as assessed by single cell gel electrophoresis (comet assay). Free Radic Biol Med 30(6): 679-685.

Duell E J, Holly E A, Bracci P M, Wiencke J K, Kelsey K T (2002) A population-based study of the Arg399Gln polymorphism in X-ray repair cross-complementing group 1 (XRCC1) and risk of pancreatic adenocarcinoma. Cancer Res 62(16): 4630-5636.

Duell E J, Wiencke J K, Cheng T J, Varkonyi A, Zuo Z F et al. (2000) Polymorphisms in the DNA repair genes XRCC1 and ERCC2 and biomarkers of DNA damage in human blood mononuclear cells. Carcinogenesis 21(5): 965-971.

Engelward B, Dreslin A, Christensen J, Huszar D, Kurahara C et al. (1996) Repair deficient 3-methyladenine DNA glycosylase homozygous mutant mouse cells have increased sensitivity to alkylation induced chromosome damage and cell killing. EMBO J. 15: 945-952.

Engelward B P, Boosalis M S, Chen B J, Deng Z, Siciliano M J et al. (1993) Cloning and characterization of a mouse 3-methyladenine/7-methylguanine/3-methylguanine DNA glycosylase cDNA whose gene maps to chromosome 11. Carcinogenesis 14(2): 175-181.

Engelward B P, Allan J M, Dreslin A J, Kelly J D, Gold B et al. (1998) A chemical and genetic approach together define the biological consequences of 3-methyladenine lesions in the mammalian genome. J Biol Chem 273: 5412-5418.

Engelward B P, Weeda G, Wyatt M D, Broekhof J L M, de Wit J et al. (1997) Base excision repair deficient mice lacking the Aag alkyladenine DNA glycosylase. Proc Natl Acad Sci USA 94: 13087-13092.

Evans A R, Kelley M R, etc. (2000) "Going APE over ref-1." *Mutant Res.* 2000; Volume 461|2:83-108.

Fairbairn D W, Olive P L, O'Neill K L (1995) The comet assay: a comprehensive review. Mutat Res 339(1): 37-59.

Fire, Mello, et al. (1998) "Potent and specific genetic interference by double-stranded RNA in *Caenorhabditis elegans.*" *Nature.* Volume 391:806-811.

Fishel M L, et al. (2007) "Manipulation of base excision repair to sensitize ovarian cancer cells to alkylating agent temozolomide." *Clin Cancer Res.* Volume 13|1:260-267.

Fishel, Melissa L., Mark R. Kelley, et al. (2008) "Knockdown of the DNA repair and redox signaling protein Ape1/Ref-1 blocks ovarian cancer cell and tumor growth." *DNA Repair (Amst).* Volume 712: 177-186.

Fishel R, Lescoe M K, Rao M R S, Copeland N G, Jenkins N A et al. (1993) The human mutator gene homolog MSH2 and its association with hereditary nonpolyposis cancer. Cell 75: 1027-1038.

Flaim C J, Chien S, Bhatia S N (2005) An extracellular matrix microarray for probing cellular differentiation. Nat Methods 2(2): 119-125.

Folch A, Toner M (1998) Cellular micropatterns on biocompatible materials. Biotechnol Prog 14(3): 388-392.

Fortini, Dogliotti E. et al. (1996) "Analysis of DNA alkylation damage and repair in mammalian cells by the comet assay." *Mutagenesis.* Volume 11|2.

Friedberg E C, Walker G C, Siede W, Wood R D, Schultz R A et al. (2006) DNA Repair and Mutagenesis. Washington, D.C.: ASM Press.

Frosina, G. (2001) "Counteracting spontaneous transformation via overexpression of ratelimitingvDNA base excision repair enzymes." *Carcinogenesis.* Volume 22|9:1335-1341.

Fry, Samson, et al. "Genomic predictors of interindividual differences in response to DNA damaging agents." *Genes and Development.* Volume 22:2621-2626.

Gedik, Catherine M., Andrew R. Collins, et al. (2002) "Oxidative stress in humans: validation of biomarkers of DNA damage." *Carcinogenesis.* Volume 23|9:1441-1446.

Glassner B J, Weeda G, Allan J M, Broekhof J L, Carls N H et al. (1999) DNA repair methyltransferase (Mgmt) knockout mice are sensitive to the lethal effects of chemotherapeutic alkylating agents. Mutagenesis 14: 339-347.

Goode, Ellen L., John D. Potter, et al. (2002) "Polymorphisms in DNA Repair Genes and Associations with Cancer Risk." *Cancer Epidemiology, Biomarkers & Prevention.* Vol. 11: 1513-1530.

Gopalakrishna P, Khar A (1995) Comet assay to measure DNA damage in apoptotic cells. J Biochem Biophys Methods 30(1): 69-73.

Hammarback J A, McCarthy J B, Palm S L, Furcht L T, Letourneau P C (1988) Growth cone guidance by substrate-bound laminin pathways is correlated with neuron-to-pathway adhesivity. Dev Biol 126(1): 29-39.

Han J, Hendzel M J, Allalunis-Turner J (2006) Quantitative analysis reveals asynchronous and more than DSB-associated histone H2AX phosphorylation after exposure to ionizing radiation. Radiat Res 165(3): 283-292.

Hartley K O, Gell D, Smith G C, Zhang H, Divecha N et al. (1995) DNA-dependent protein kinase catalytic subunit: a relative of phosphatidylinositol 3-kinase and the ataxia telangiectasia gene product. Cell 82(5): 849-856.

Hartmann A, Agurell E, Beevers C, Brendler-Schwaab S, Burlinson B et al. (2003) Recommendations for conducting the in vivo alkaline Comet assay. 4th International Comet Assay Workshop. Mutagenesis 18(1): 45-51.

Hartman, Andreas (Novartis Pharma), et al. (2001) "Use of the alkaline comet assay for industrial genotoxicity screening: comparative investigation with the micronucleus test." *Food and chemical toxicology.* Volume 39|8:843-858.

Hartman, Andreas (Novartis Pharma), et al. (2004) "The in vivo comet assay: use and status in genotoxicity testing." *Mutagenesis,* Volume 19|1:51-59.

Hawkins, Dawkins, et al. (2006) "Radiation therapy for hepatocellular carcinoma: from palliation to cure." *Cancer.* Volume 106|8:1653-63.

Helleday T (2003) Pathways for mitotic homologous recombination in mammalian cells. Mutation Res 532(1-2): 103-115.

Helleday T, Petermann E, Lundin C, Hodgson B, Sharma R A. (2008) DNA repair pathways as targets for cancer therapy. *Nat Rev Cancer*. Volume 3:193-204.

Heller M J (1996) An active microelectronics device for multiplex DNA analysis. IEEE Eng Med Biol 15(2): 100-104.

Hendricks C A, Engelward B P (2004) "Recombomice": the past, present, and future of recombination-detection in mice. DNA Repair (Amst) 3(10): 1255-1261.

Hendricks C A, Razlog M, Matsuguchi T, Goyal A, Brock A L et al. (2002) The *S. cerevisiae* Mag1 3-methyladenine DNA glycosylase modulates susceptibility to homologous recombination. DNA Repair 1(8): 645-659.

Hendricks C A, Almeida K H, Stitt M S, Jonnalagadda V S, Rugo R E et al. (2003) Spontaneous mitotic homologous recombination at an enhanced yellow fluorescent protein (EYFP) cDNA direct repeat in transgenic mice. Proc Natl Acad Sci USA 100(11): 6325-6330.

Hodneland C D, Lee Y S, Min D H, Mrksich M (2002) Selective immobilization of proteins to self-assembled monolayers presenting active site-directed capture ligands. Proc Natl Acad Sci USA 99(8): 5048-5052.

Horvathova E, Slamenova D, Gabelova A (1999) Use of single cell gel electrophoresis (comet assay) modifications for analysis of DNA damage. Gen Physiol Biophys 18 Spec No: 70-74.

Hoffmann, Guenter Speit, et al. (2005) "The effect of smoking on DNA effects in the comet assay: a meta-analysis." *Mutagenesis*. Volume. 2016: 445-466.

Jackman R (1998) Fabricating large arrays of microwells with arbitrary dimensions and filling them using discontinuous dewetting. Anal Chem 70: 2280-2287.

Jiang Y, Guo C, Vasko M R, Kelley M R. (2008) "Implications of apurinic/apyrimidinic endonuclease in reactive oxygen signaling response after cisplatin treatment of dorsal root ganglion neurons." *Cancer Res*. Volume 68|15:6425-34.

Jonnalagadda V S, Matsuguchi T, Engelward B P (2005) Interstrand crosslink-induced homologous recombination carries an increased risk of deletions and insertions. DNA Repair (Amst) 4(5): 594-605.

Kapur R (1999) Streamlining the drug discovery process by integrating miniaturization, high throughput screening, high content screening and automation on the cellchip system. Biomed Microdev 2: 99-110.

Khetani S R, Szulgit G, Del Rio J A, Barlow C, Bhatia S N (2004) Exploring interactions between rat hepatocytes and nonparenchymal cells using gene expression profiling. Hepatology 40(3): 545-554.

Kiskinis E, Suter W, Hartmann A (2002) High throughput Comet assay using 96-well plates. Mutagenesis 17(1): 37-43.

Kiziltepe T, Yan A, Dong M, Jonnalagadda V S, Dedon P C et al. (2005) Delineation of the chemical pathways underlying nitric oxide-induced homologous recombination in mammalian cells. Chem Biol 12(3): 357-369.

Klaude M, Eriksson S, Nygren J, Ahnstrom G (1996) The comet assay: mechanisms and technical considerations. Mutat Res 363(2): 89-96.

Kohn K W, Grimek-Ewig R A (1973) Alkaline elution analysis, a new approach to the study of DNA single-strand interruptions in cells. Cancer Res 33(8): 1849-1853.

Kovalchuk O, Burke P, Besplug J, Slovack M, Filkowski J et al. (2004) Methylation changes in muscle and liver tissues of male and female mice exposed to acute and chronic low-dose X-ray-irradiation. Mutat Res 548(1-2): 75-84.

Larson K, Sahm J, Shenkar R, Strauss B (1985) Methylation-induced blocks to in vitro DNA replication. Mutat Res 150: 77-84.

Lee K B, Park S J, Mirkin C A, Smith J C, Mrksich M (2002) Protein nanoarrays generated by dip-pen nanolithography. Science 295(5560): 1702-1705.

Lee M, Kumar A, Sukumaran S M, Hogg M G, Clark D S, Dordick J S (2008) Three-dimensional cellular microarray for high-throughput toxicology assays. PNAS 105: 59-63.

Lee M, Park C B, Dordick J S, Clark D S (2005) Metabolizing enzyme toxicology assay chip (MetaChip) for high-throughput microscale toxicity analyses. PNAS 102: 983-987.

Lei Y C, Hwang S J, Chang C C, Kuo H W, Luo J C et al. (2002) Effects on sister chromatid exchange frequency of polymorphisms in DNA repair gene XRCC1 in smokers. Mutat Res 519(1-2): 93-101.

Leong, Jen, et al. (2009) "Single-Cell Patterning and Adhesion on Chemically Engineered Poly(dimethylsiloxane) Surface." *Langmuir*. [published on web].

Li C Q, Pang B, Kiziltepe T, Trudel L J, Engelward B P et al. (2006) Threshold effects of nitric oxide-induced toxicity and cellular responses in wild-type and p53-null human lymphoblastoid cells. Chem Res Toxicol 19(3): 399-406.

Liu L, Taverna P, Whitacre C M, Chatterjee S, Gerson S L. (1999) "Pharmacologic disruption of base excision repair sensitizes mismatch repair-deficient and -proficient colon cancer cells to methylating agents." *Clin Cancer Res*. Volume 9|5:2908.

Liu L, Gerson S L. (2004) "Therapeutic impact of methoxyamine: blocking repair of abasic sites in the base excision repair pathway." *Curr Opin Investig Drugs*. Volume 5|6:623-627.

Liu V A, Shatia S N (2002) Three-dimensional photopatterning of hydrogels containing living cells. Biomed Microdev 4: 257-266.

Liu V A, Jastromb W E, Bhatia S N (2002) Engineering protein and cell adhesivity using PEO-terminated triblock polymers. J Biomed Mater Res 60(1): 126-134.

Lombard D B, Beard C, Johnson B, Marciniak R A, Dausman J et al. (2000) Mutations in the WRN gene in mice accelerate mortality in a p53-null background. Mol Cell Biol 20(9): 3286-3291.

Longo D, Hasty J (2006) Imaging gene expression: tiny signals make a big noise. Nat Chem Biol 2(4): 181-182.

Lowe S W, Schmitt E M, Smith S W, Osborne B A, Jacks T (1993) p53 is required for radiation-induced apoptosis in mouse thymocytes. Nature 362(6423): 847-849.

MacBeath G, Schreiber S L (2000) Printing proteins as microarrays for high-throughput function determination. Science 289(5485): 1760-1763.

MacPhail S H, Banath J P, Yu Y, Chu E, Olive P L (2003) Cell cycle-dependent expression of phosphorylated histone H2AX: reduced expression in unirradiated but not X-irradiated G1-phase cells. Radiat Res 159(6): 759-767.

Madhusudan, Hickson, et al. (2005) "Isolation of a small molecule inhibitor of DNA base excision repair." *Nucleic Acids Research*. Volume 33|15.

Maher, Robyn L., Aarthy C. Vallur, Joyce A. Feller, Linda B. Bloom. (2007) "Slow base excision by human alkyladenine DNA glycosylase limits the rate of formation of AP sites and AP endonuclease 1 does not stimulate base excision." *DNA Repair*. Volume 6|1:71-81.

Marcon, Crebelli R, et al. (2003) "Assessment of individual sensitivity to ionizing radiation and DNA repair efficiency in a healthy population." *Mutat. Res*. Volume 541|1:1-8.

Marlin, David J., Pat A. Harris, et al. (2004) "Application of the Comet Assay for Investigation of Oxidative DNA Damage in Equine Peripheral Blood Mononuclear Cells." *The American Society for Nutritional Sciences J. Nutr.* Volume 134.

Martin B D (1998) Direct protein microarray fabrication using a hydrogel "stamper". Langmuir 14: 3971-3975.

Matusue T, Matsumoto N, Uchida I (1997) Rapid micropatterning of living cells by repulsive dielectrophoretic force. Electrochemica Acta 42: 3251-3256.

McKenna D J, McKelvey-Martin, et al. (2008) "Potential use of the comet assay in the clinical management of cancer." *Mutagenesis.* Volume 23|(3):183-90.

McKeown S R., V J McKelvey-Martin, et al. (2003) "Potential use of the alkaline comet assay as a predictor of bladder tumour response to radiation." *British Journal of Cancer.* Volume 89:2264-2270.

Memisoglu A, Samson L (2000) Base excision repair in yeast and mammals. Mutat Res 451: 39-51.

Michel B, Flores M J, Viguera E, Grompone G, Seigneur M et al. (2001) Rescue of arrested replication forks by homologous recombination. Proc Natl Acad Sci USA 98(15): 8181-8188.

Moeller, Khademhossein, et al. (2008) "A microwell array system for stem cell culture." *Biomaterials.* Volume 29|6: 752-763.

Moller P (2006) The alkaline comet assay: towards validation in biomonitoring of DNA damaging exposures. Basic Clin Pharmacol Toxicol 98(4): 336-345.

Moller P. (2006) "Assessment of reference values for DNA damage detected by the comet assay in human blood cell DNA." *Mutat Res.* Volume 612|84-104.

Mrksich M, Chen C S, Xia Y, Dike L E, Ingber D E et al. (1996) Controlling cell attachment on contoured surfaces with self-assembled monolayers of alkanethiolates on gold. Proc Natl Acad Sci USA 93(20): 10775-10778.

Mueller, Seeber, et al. (1998) "Drug resistance and DNA repair in leukaemia." *Cytotechnology.* Volume 27:175-185.

Nathan C (2002) Points of control in inflammation. Nature 420(6917): 846-852.

Olive, Peggy. (2007) "Impact of the comet assay in radiobiology." *Mutation Research.* Volume 681|1:13-2.

Olive P L, Banath J P (2006) The comet assay: a method to measure DNA damage in individual cells. Nature Protocols 1(1): 23-29.

Olive P L, Wlodek D, Banath J P (1991) DNA double-strand breaks measured in individual cells subjected to gel electrophoresis. Cancer Res 51(17): 4671-4676.

Olive P L, Frazer G, Banath J P (1993) Radiation-induced apoptosis measured in TK6 human B lymphoblast cells using the comet assay. Radiat Res 136(1): 130-136.

Olive P L, Wlodek D, Durand R E, Banath J P (1992) Factors influencing DNA migration from individual cells subjected to gel electrophoresis. Exp Cell Res 198(2): 259-267.

Orlow, Irene, Valerie W. Rusch, et al. (2005) "DNA Damage and Repair Capacity in Patients With Lung Cancer: Prediction of Multiple Primary Tumors." *Journal of Clinical Oncology.* Volume 26|21:3560-3566.

Oshida, Miyamoto, et al. (2008) "An in vivo comet assay of multiple organs (liver, kidney and bone marrow) in mice treated with methyl methanesulfonate and acetaminophen accompanied by hematology and/or blood chemistry." *J Toxicol Sci.* Volume 33|5.

Ostling O, Johanson K J (1984) Microelectrophoretic study of radiation-induced DNA damages in individual mammalian cells. Biochem Biophys Res Commun 123(1): 291-298.

Paz-Elizur T., Livneh, et al. (2008) "DNA repair of oxidative DNA damage in human carcinogenesis: Potential application for cancer risk assessment and prevention." *Cancer Letters.* Volume 266.

Pease A C, Solas D, Sullivan E J, Cronin M T, Holmes C P et al. (1994) Light-generated oligonucleotide arrays for rapid DNA sequence analysis. Proc Natl Acad Sci USA 91(11): 5022-5026.

Pichierri P, Franchitto A, Mosesso P, Palitti F (2001) Werner's syndrome protein is required for correct recovery after replication arrest and DNA damage induced in S-phase of cell cycle. Mol Biol Cell 12(8): 2412-2421.

Pincheira, et al. (2008) "Hepatocytes, rather than leukocytes reverse DNA damage in vivo induced by whole body g-irradiation mice, as shown by the alkaline comet assay." *Biol Res.* Volume 41.

Piperakis S M, Petrakou E, Tsilimigaki S (2000) Effects of air pollution and smoking on DNA damage of human lymphocytes. Environ Mol Mutagen 36(3): 243-249.

Pouget J P, Douki T, Richard M J, Cadet J (2000) DNA damage induced in cells by gamma and UVA radiation as measured by HPLC/GC-MS and HPLC-EC and Comet assay. Chem Res Toxicol 13(7): 541-549.

Pouget J P, Ravanat J L, Douki T, Richard M J, Cadet J (1999) Measurement of DNA base damage in cells exposed to low doses of gamma-radiation: comparison between the HPLC-EC and comet assays. Int J Radiat Biol 75(1): 51-58.

Rogakou E P, Pilch D R, Orr A H, Ivanova V S, Bonner W M (1998) DNA double-stranded breaks induce histone H2AX phosphorylation on serine 139. J Biol Chem 273(10): 5858-5868.

Rothkamm K, Lobrich M (2003) Evidence for a lack of DNA double-strand break repair in human cells exposed to very low x-ray doses. Proc Natl Acad Sci USA 100(9): 5057-5062.

Roti Roti J L, Wright W D (1987) Visualization of DNA loops in nucleoids from HeLa cells: assays for DNA damage and repair. Cytometry 8(5): 461-467.

Ruchirawat M, Navasumrit P, Settachan D, Autrup H (2006a) Environmental impacts on children's health in Southeast Asia: genotoxic compounds in urban air. Ann NY Acad Sci 1076: 678-690.

Ruchirawat M, Settachan D, Navasumrit P, Tuntawiroon J, Autrup H (2006b) Assessment of potential cancer risk in children exposed to urban air pollution in Bangkok, Thailand. Toxicol Lett.

Rydberg B (1975) The rate of strand separation in alkali of DNA of irradiated mammalian cells. Radiat Res 61(2): 274-287.

Rydberg B (2000) Radiation-induced heat-labile sites that convert into DNA double-strand breaks. Radiat Res 153(6): 805-812.

Ryk C, Hou S, et al. (2008) "Influence of DNA repair gene polymorphisms on the initial repair of MMS-induced DNA damage in human lymphocytes as measured by the alkaline com.

Sasaki Y F, Sekihashi K, Izumiyama F, Nishidate E, Saga A et al. (2000) The comet assay with multiple mouse organs: comparison of comet assay results and carcinogenicity with 208 chemicals selected from the IARC monographs and U.S. NTP Carcinogenicity Database. Crit Rev Toxicol 30(6): 629-799.

Schmezer, Peter, Helmut Bartsch, et al. (2001) "Rapid screening assay for mutagen sensitivity and DNA repair capacity in human peripheral blood lymphocytes." *Mutagenesis.* Volume 16|1:25-30.

Seetharaman S, Zivarts M, Sudarsan N, Breaker R R (2001) Immobilized RNA switches for the analysis of complex chemical and biological mixtures. Nat Biotechnol 19(4): 336-341.

Seglen, P. O. (1976) "Preparation of isolated rat liver cells" *Methods Biol*. Volume 1976|13:29-83.

Seiple, Stivers, et al. (2008) "Potent Inhibition of Human Apurinic/Apyrimidinic Enonuclease 1 by Arylstibonic Acids." *Molecular Pharmacology*. Volume 72:669-677.

Shahidi M, Mozdarani H, Bryant P E. (2007) "Radiation sensitivity of leukocytes from healthy individuals and breast cancer patients as measured by the alkaline and neutral comet assay." *Cancer Lett*. Volume 257|2:263-73.

Sharma R A, Farmer P B (2004) Biological relevance of adduct detection to the chemoprevention of cancer. Clin Cancer Res 10(15): 4901-4912.

Shiloh Y (2003) ATM and related protein kinases: safeguarding genome integrity. Nat Rev Cancer 3(3): 155-168.31.

Siede and Walker. (1995) *DNA Repair and Mutagenesis*. Published by ASM Press.

Simeonov, David Wilson, et al. (2009) "Identification and characterization of inhibitors of human apurinic/apyrimidinic endonuclease APE1." [Under Review].

Singh N P, McCoy M T, Tice R R, Schneider E L (1988) A simple technique for quantitation of low levels of DNA damage in individual cells. Exp Cell Res 175(1): 184-191.

Singh R, Farmer P B (2006) Liquid chromatography-electrospray ionization-mass spectrometry: the future of DNA adduct detection. Carcinogenesis 27(2): 178-196.

Singhvi R, Stephanopoulos G, Wang D I C (1994) Effects of substratum morphology on cell physiology. Biotech Bioeng 43: 764-771.

Slupphaug G, Kavli B, Krokan H E (2003) The interacting pathways for prevention and repair of oxidative DNA damage. Mutat Res 531(1-2): 231-251.

Smith S A, Engelward B P (2000) In vivo repair of methylation damage in Aag 3-methyladenine DNA glycosylase null mouse cells. Nucl Acids Res 28(17): 3294-3300.

Spanswick, Victoria, John Hartley, et al. (2008) "Measurement of Drug-Induced DNA Interstrand Crosslinking Using the Single-Cell Gel Electrophoresis Assay." *Methods in Molecular Medicine*. Vol 28: 143-154.

Speit, Guenter, Heikie Hoffmann, et al. (2003) "Investigations on the effect of cigarette smoking in the comet assay." *Mutation Research*. Volume 542:33-42.

Spek E J, Vuong L N, Matsuguchi T, Marinus M G, Engelward B P (2002) Nitric oxide-induced homologous recombination in *Escherichia coli* is promoted by DNA glycosylases. J Bacteriol 184(13): 3501-3507.

Spek E J, Wright T L, Stitt M S, Taghizadeh N R, Tannenbaum S R et al. (2001) Recombinational repair is critical for survival of *Escherichia coli* exposed to nitric oxide. J Bacteriol 183(1): 131-138.

Stamato T D, Denko N (1990) Asymmetric field inversion gel electrophoresis: a new method for detecting DNA double-strand breaks in mammalian cells. Radiat Res 121(2): 196-205.

Staresincic L, Schärer O D, et al. (2009) "Coordination of dual incision and repair synthesis in human nucleotide excision repair." *EMBO J*. March 12.

Sykes P J, Hooker A M, Harrington C S, Jacobs A K, Kingsbury L et al. (1998) Induction of somatic intrachromosomal recombination inversion events by cyclophosphamide in a transgenic mouse model. Mutation Res 397(2): 209-219.

Synowiec E, Stefanska J, Morawiec Z, Blasiak J, Wozniak K. (2008) "Association between DNA damage, DNA repair genes variability and clinical characteristics in breast cancer patients." *Mutat Res*. Volume 648|1-2:65-72.

Takayama S, Reed J C, Homma S (2003) Heat-shock proteins as regulators of apoptosis. Oncogene 22(56): 9041-9047.

Takayama S, McDonald J C, Ostuni E, Liang M N, Kenis P J et al. (1999) Patterning cells and their environments using multiple laminar fluid flows in capillary networks. Proc Natl Acad Sci USA 96(10): 5545-5548.

Tanaka K, Miura N, Satokata I, Miyamoto I, Yoshida M C et al. (1990) Analysis of a human DNA excision repair gene involved in group A xeroderma pigmentosum and containing a zinc-finger domain. Nature 348(6296): 73-76.

Taverna P, et al. (2001) "Methoxyamine potentiates DNA single strand breaks and double strand breaks induced by temozolomide in colon cancer cells." *Mutat Res*. Volume 485|4:269-281.

Trzeciak A R, Michele K. Evans, et al. (2008) "Age, sex, and race influence single-strand break repair capacity in a human population." *Free Radical Biology and Medicine*. Volume 45|12:1631-1641.

Trzeciak, Evans, et al. (2008) "A Modified Alkaline Comet Assay for Measuring DNA Repair Capacity in Human Populations." *Radiat. Res*. Volume 169:110-121.

Tuntawiroon J, Mahidol C, Navasumrit P, Autrup H, Ruchirawat M (2006) Increased health risk in Bangkok children exposed to polycyclic aromatic hydrocarbons from traffic-related sources. Carcinogenesis.

Vogelstein B, Kinzler K W (2004) Cancer genes and the pathways they control. Nat Med 10(8): 789-799.

Vogelstein B, Pardoll D M, Coffey D S (1980) Supercoiled loops and eucaryotic DNA replication. Cell 22(1 Pt 1): 79-85.

Vorobyova N Y, Osipova A N, Pelevina I I. (2007) "Sensitivity of peripheral blood lymphocytes of pilots and astronauts to gamma-radiation: induction of double-stranded DNA breaks." Volume 144|4:523-6.

Wang, Luo, Kelley. (2004) "Human apurinic endonuclease 1 (APE1) expression and prognostic significance in osteosarcoma: Enhanced sensitivity of osteosarcoma to DNA damaging agents using silencing RNA APE1 expression inhibition." *Molecular Cancer Therapeutics*. Volume 316.

Wiktor-Brown D M, Hendricks C A, Olipitz W, Engelward B P (2006a) Age-dependent accumulation of recombinant cells in the mouse pancreas revealed by in situ fluorescence imaging. Proc Natl Acad Sci USA 103(32): 11862-11867.

Wiktor-Brown D M, Hendricks C A, Olipitz W, Rogers A B, Engelward B P (2006b) Applications of Fluorescence for Detecting Rare Sequence Rearrangements In Vivo. Cell Cycle 5(23).

Wlodek D, Olive P L (1990) Physical basis for detection of DNA double-strand breaks using neutral filter elution. Radiat Res 124(3): 326-333.

Wlodek D, Banath J, Olive P L (1991) Comparison between pulsed-field and constant-field gel electrophoresis for measurement of DNA double-strand breaks in irradiated Chinese hamster ovary cells. Int J Radiat Biol 60(5): 779-790.

Woodcock, Janet, FDA's Deputy Commissioner for Operations. (2004) "Innovation/Stagnation: Challenge and Opportunity on the Critical Path to New Medical Products." *FDA News Release*.

Wooster R, Neuhausen S L, Mangion J, Quirk Y, Ford D et al. (1994) Localization of a breast cancer susceptibility gene, BRCA2, to chromosome 13q12-13. Science 265(5181): 2088-2090.

Xu Y, Ashley T, Brainerd E E, Bronson R T, Meyn M S et al. (1996) Targeted disruption of ATM leads to growth retardation, chromosomal fragmentation during meiosis, immune defects, and thymic lymphoma. Genes & Dev 10(19): 2411-2422.

Yaghi, et al. (1998) "Comparative mutational spectra of the nitrogen mustard chlorambucil and its half-mustard analogue in Chinese hamster AS52 cells." *Mutation Research* 401:153-164 et assay." Environ Mol. Mutagen. Volume 49|9:669-75.

Yousaf M N, Houseman B T, Mrksich M (2001) Using electroactive substrates to pattern the attachment of two different cell populations. Proc Natl Acad Sci USA 98(11): 5992-5996.

Zhang, H, Buchholz T A, Hancock D, Spitz M R, Wu X. (2000) "Gamma-radiation-induced single cell DNA damage as a measure of susceptibility to lung cancer: a preliminary report." *Int J. Oncol.* Volume 17|2:399-404.

Ziauddin J, Sabatini D M (2001) Microarrays of cells expressing defined cDNAs. Nature 411(6833): 107-110.

Zou and Maitra. (2008) "Small-molecule inhibitor of the AP endonuclease 1/REF-1 E3330 inhibits pancreatic cancer cell growth and migration." *Mol Cancer Ther.* Volume 7|7:2012.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for analyzing a nucleic acid, comprising:
   disposing at least one cell having DNA to be analyzed into each of a plurality of spatially-defined cell capture locations formed in a solidified matrix material;
   positioning an overlay over the matrix material;
   utilizing the overlay to apply at least one reagent to at least one cell capture location of the plurality of spatially defined cell capture locations or a portion of the matrix material; and
   analyzing at least one cell following application of the reagent for nucleic acid fragmentation.

2. The method of claim 1, further comprising:
   removing the overlay from the matrix material;
   performing electrophoresis on the plurality of cells; and
   analyzing nucleic acid fragmentation based on comet parameters resulting from nucleic acid migration.

3. The method of claim 1 wherein the step of utilizing the overlay further comprises utilizing an overlay having at least one reagent disposed thereon to apply the reagent by contact with the cells.

4. The method of claim 1 wherein the step of utilizing the overlay further comprises utilizing an overlay having at least one opening to allow at least one reagent to be passed therethrough.

5. The method of claim 1, wherein the matrix material is an agarose gel.

6. The method of claim 1, wherein a thickness of the solidified matrix material is in the range of about 10 microns to about 300 microns.

7. The method of claim 1, wherein a depth of the plurality of spatially-defined cell capture locations is in the range of about 4 micrometers to about 20 micrometers.

8. The method of claim 1, wherein the step of disposing cells in the spatially-defined cell capture locations further comprises applying a fluid comprising the cells onto the surface of the matrix material.

9. The method of claim 1, wherein the step of disposing cells in the spatially-defined cell capture locations further comprises printing cells onto the matrix material.

10. The method of claim 1, wherein the step of applying at least one reagent to the cells further comprises applying multiple, different reagents to the cells.

11. The method of claim 1, further comprising moving the overlay with respect to the matrix material while applying at least one reagent to the cells.

12. The method of claim 1, further comprising:
    applying a second matrix material to the first matrix material after cells have been applied over the surface of the first matrix material; and
    allowing the second matrix material to solidify to approximately maintain a location of the cells with respect to the first matrix material.

13. The method of claim 1, further comprising:
    placing a divider over the matrix material; and
    adding a second matrix material having a plurality of cells disposed therein above the divider.

14. The method of claim 1, further comprising:
    applying a matrix material to a substrate, the matrix material being the matrix material in which a plurality of spatially-defined cell capture locations that receive at least one cell having DNA to be analyzed are formed;
    contacting the matrix material with a template having a pattern of protuberances to form the plurality of spatially-defined cell capture locations in the matrix material; and
    removing the template from the matrix material.

15. A method for manufacturing a nucleic acid analysis device, comprising:
    applying a matrix material to a substrate, the matrix material including an agarose gel;
    contacting the matrix material with a template having a pattern of protuberances to form spatially-defined cell capture locations in the matrix material;
    removing the template from the matrix material; and
    allowing the matrix material to solidify such that a plurality of spatially-defined cell capture locations are formed therein at locations based on the pattern of protuberances, each cell capture location of which is configured to receive one or more cells having DNA to be analyzed.

16. The method of claim 15, wherein a thickness of the solidified matrix material is in the range of about 10 microns to about 300 microns.

17. The method of claim 15, wherein a depth of the plurality of spatially-defined cell capture locations is in the range of about 4 micrometers to about 20 micrometers.

* * * * *